United States Patent [19]
Sumi et al.

[11] Patent Number: 5,495,771
[45] Date of Patent: Mar. 5, 1996

[54] ELASTICITY MEASURING METHOD AND ELASTICITY MEASURING APPARATUS

[75] Inventors: Chikayoshi Sumi, Saitama; Kiyoshi Nakayama, 2-12-9, Honcho, Koganei-shi, Tokyo, 184, both of Japan

[73] Assignees: Kiyoshi Nakayama, Tokyo; Fujitsu Limited, Kawasaki, both of Japan

[21] Appl. No.: 233,420

[22] Filed: Apr. 28, 1994

[30] Foreign Application Priority Data

Aug. 12, 1993 [JP] Japan .................... 5-200801

[51] Int. Cl.$^6$ .................................................. G01D 7/02
[52] U.S. Cl. .................................. 73/789; 73/573
[58] Field of Search ........................... 73/787, 789, 573, 73/762, 508, 570

[56] References Cited

U.S. PATENT DOCUMENTS

| | | | |
|---|---|---|---|
| 4,099,408 | 8/1978 | Ludwigson | 73/834 |
| 4,304,135 | 12/1981 | Peterson et al. | 73/799 |
| 4,694,698 | 9/1987 | Miyajima | 73/570 |
| 4,781,056 | 11/1988 | Noel et al. | 73/508 |
| 5,335,661 | 9/1994 | Koblanski | 73/599 |

Primary Examiner—Richard Chilcot
Assistant Examiner—Max Noori
Attorney, Agent, or Firm—Staas & Halsey

[57] ABSTRACT

There are provided an elasticity measuring method of measuring an elastic constant of elasticity of an elastic body, for example, an elastic rubber, an organism or a living body, etc., which is soft and rather incompressible, by means of measuring an internal strain using energy such as ultrasounds, an X-ray, and magnetism, where the elastic constant includes, for example, typically shear modulus, Young's modulus, etc.; and an elasticity measuring apparatus adapted to practice such an elasticity measuring method. According to such method and apparatus, the elastic constant distribution within the subject is detected only through measuring the strain distribution within the subject, without measuring the stress distribution. The elasticity measuring method is of detecting the ratio of elastic value-to-elastic value, which are representative of levels of elasticity involved in a reference point on a predetermined straight line extending inside of a subject and a predetermined observation point on the straight line, respectively, by means of detecting the ratio of strain-to-strain, which are involved in said referencepoint and said observation point, respectively, with respect to a direction toward which the straight line extends.

28 Claims, 25 Drawing Sheets

$$\frac{G(x)}{G(A)} = \frac{G(x-dx)}{G(A)} \quad (1-4)$$

$$x = A$$
$$s = InGo$$

Fig. 6

ELASTICITY MEASURING METHOD AND ELASTICITY MEASURING APPARATUS

BACKGROUND OF THE INVENTION

1. Field of the Invention

The present invention relates to an elasticity measuring method of measuring a value representative of a level of elasticity of an elastic body, for example, an elastic rubber, an organism or a living body, etc., which is soft and rather incompressible, by means of measuring an internal strain using energy such as ultrasounds, an X-ray, and magnetism, where said value may be referred to as "elastic value" or "elastic constant" hereinafter, and includes, for example, typically shear modulus, Young's modulus, etc.; and an elasticity measuring apparatus, which is adapted to practice such an elasticity measuring method, and to be incorporated into, for example, a non-destructive inspection equipment, an image diagnostic system in which the elastic constant of the human body is measured, and upon being regarded as an organized body, an organized body diagnosis is implemented, and the like.

2. Description of the Related Art

Hitherto, the elastic constant of a uniform quality of elastic rubber or the like is determined in such a manner that a test material shaped as a board is set up to a tension tester to measure both stress and strain, so that the elastic constant is calculated. With regard to a living body, for example, in case of a checkup for breast cancer, a doctor examines stiffness of the object through the palpation.

With respect to industrial products such as the elastic rubber, it is theoretically possible, after they are processed in a format of the product such as a tire or the like, to conduct the diagnosis as to whether the inside of the product is provided with a uniform elasticity. This will be implemented in such a way that the force is applied from the outside to the industrial product to induce the strain, and at that time the stress distribution of the product and the strain distribution of the inside thereof are all measured so that the distribution of the elastic constant can be detected and visibly displayed on a display unit. However, indeed, it is very difficult to measure the stress distribution of the surface of the products as well as the stress distribution of the inside of the products. Thus, it is actually almost impossible to implement the diagnosis as to whether the inside of the product is provided with a uniform elasticity.

Further, the palpation practiced for a living body involves problems, because it depends on a doctor's sense or feeling and thus lacks a determinability. Furthermore, it is difficult to diagnose a lesion organization, such as the liver cancer, which hides far back in the internal organs. Still further, even if it is desired that the distribution of the elastic constant is detected in accordance with the stress distribution of a surface of the living body and the strain distribution of the inside thereof, it is more difficult, in comparison with that in case of the industrial products, to measure the stress distribution of a surface of the living body. For example, now, even if it is desired that the elastic constant of the liver tissue is detected in accordance with the strain of the liver due to the pulsation of the heart, it is impossible to measure the stress distribution of the liver. It may be considered that a low frequency of motion is generated by means of applying from the outside the vibration with a predetermined force and a predetermined velocity using a vibrator-like something, or a static deformation is provided by means of pushing using a spread board-like configuration of something. However, it is almost impossible to measure the stress distribution of the inside and it is even difficult to measure the stress distribution of a skin surface of the living body.

SUMMARY OF THE INVENTION

In view of the foregoing, it is therefore an object of the present invention to provide an elasticity measuring method capable of determining an elastic constant distribution of the inside of the subject through only a measurement of the strain distribution of the inside of the subject, without necessity of measurement of the stress distribution, and an elasticity measuring apparatus, which is adapted to practice such an elasticity measuring method.

To achieve the above-mentioned objects, according to the present invention, there is provided the first elasticity measuring method of detecting the ratio of elastic value-to-elastic value, which are representative of levels of elasticity involved in a reference point on a predetermined straight line extending inside of a subject and a predetermined observation point on the straight line, respectively, by means of detecting the ratio of strain-to-strain, which are involved in said reference point and said observation point, respectively, with respect to a direction toward which the straight line extends.

Here, it is noted that the above-referenced terminology "elastic value" may be representative of a level of elasticity, and includes in technical concept, for example, typically shear modulus $G$, Young's modulus $E$, and arithmetic operation results including those, for example, $G^2$, $E^2$, $\ln G$, $\ln E$, $aG+b$ ($a$, $b$ each constant), etc. Further, for example, as shown in the expression (23) which will be described later, there will be a case where the ratio of strains is directly equivalent to the ratio of elastic values. In such a case, according to the present invention, the aforementioned terminology "the ratio of elastic value-to-elastic value" includes in technical concept the ratio of strains also. This is the similar as to the matter of terminology such as "elastic value", "the ratio of elastic value-to-elastic value", etc., which will be described hereinafter. While the term "elastic value" implies rather variable which will take different values on the respective points inside of the subject, it happens here that such terminology is referred to as "elastic constant" which is more general term.

Further, according to the present invention, there is provided the second elasticity measuring method wherein a reference member, of which elastic value representative of a level of elasticity is known, is disposed on a reference point on a predetermined straight line extending inside of a subject; and an elastic value on a predetermined observation point on the straight line within the subject is detected on the basis of the ratio of strain-to-strain, which are involved in said reference point and said observation point, respectively, with respect to a direction toward which the straight line extends, and the elastic value of said reference member.

In the first and second elasticity measuring method as mentioned above, it is preferable that it is determined whether an absolute value of the strain on the observation point exceeds a predetermined threshold, and if the absolute value is less than the threshold, a predetermined value by which the ratio of strain-to-strain respectively involved in said reference point and said observation point is replaced is associated with said observation point, instead of said ratio of strain-to-strain.

Furthermore, according to the present invention, there is provided the third elasticity measuring method comprising the steps of:

detecting strain$\epsilon_{xx}$ (x) as to points on a predetermined straight line extending inside of a subject from a reference point A up to a predetermined observation point X, with respect to a direction toward which the straight line extends, and a differential coefficient $\epsilon_{xx}$ (x), $_x$ of the strain $\epsilon_{xx}$ (x) with respect to the direction toward which the straight line extends, and detecting an integral value of the ratio of the strain$\epsilon_{xx}$ (x) to the differential coefficient$\epsilon_{xx}$ (x),$_x$ along the straight line from the reference point A up to the observation point X, whereby the ratio of elastic value-to-elastic value, which are representative of levels of elasticity involved in the reference point A and the observation point X, respectively, is detected.

Still further, according to the present invention, there is provided the fourth elasticity measuring method wherein a reference member, of which elastic value representative of a level of elasticity is known, is disposed on a reference point A on a predetermined straight line extending inside of a subject, said method comprising the steps of:

detecting strain $\epsilon_{xx}$ (x) as to points on the straight line extending inside of the subject from the reference point A up to a predetermined observation point X, with respect to a direction toward which the straight line extends, and a differential coefficient $\epsilon_{xx}$(x), $_x$ of the strain$\epsilon_{xx}$ (x) with respect to the direction toward which the straight line extends, detecting an integral value of the ratio of the strain$\epsilon_{xx}$ (x) to the differential coefficient$\epsilon_{xx}$ (x),$_x$ along the straight line from the reference point A up to the observation point X, and detecting an elastic value on the observation point X on the basis of both the integral value and the elastic value of said reference member.

Also in the third and fourth elasticity measuring method as mentioned above, similar to the first and second elasticity measuring method, it is preferable that it is determined whether absolute values of the strain $\epsilon_{xx}$ (x) on the points x exceed a predetermined threshold, and if an absolute value of strain $\epsilon_{xx}$ (x$_0$) as to a predetermined point x$_0$ of any of the points x is less than the threshold, the ratio of the strain $\epsilon_{xx}$ (x$_0$) as to the predetermined point x$_0$ to the differential coefficient $\epsilon_{xx}$ (x$_0$),$_x$ is replaced by a predetermined value to detect the integral value.

Still further, according to the present invention, there is provided the fifth elasticity measuring method comprising the steps of:

detecting strains, $\epsilon_{xx}$ (x,y), $\epsilon_{xy}$ (x,y), $\epsilon_{yx}$ (x,y) and $\epsilon_{yy}$ (x,y) as to points (x, y) on an arbitrary route C in a predetermined two-demensional plane spreading within a subject from a reference point (A, B) up to a predetermined observation point (X,Y), and their associated differential coefficient$\epsilon_{xx}$ (x,y), $_x$ , $\epsilon_{xx}$(x,y), $_y$, $\epsilon_{xy}$ (x,y), $_x$, $\epsilon_{xy}$ (x,y), $_y$, $\epsilon_{yy}$ (x,y), $_x$, $\epsilon_{yy}$ (x,y), $_y$; and detecting a curvilinear integral value on the route C from the reference point (A, B) up to the observation point (X,Y), where the curvilinear integral value is given by the following expression $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)} \cdot$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\}_{,x}+\epsilon_{xy}(x,y)_{,y} \\ \epsilon_{yx}(x,y)_{,x}+\{\epsilon_{xx}(x,y)+2\epsilon_{yy}(x,y)\}_{,y} \end{pmatrix}$$

whereby the ratio of elastic value-to-elastic value, which are representative of levels of elasticity involved in the reference point (A, B) and the observation point (X, Y), respectively, is detected.

Still further, according to the present invention, there is provided the sixth elasticity measuring method where in a reference member, of which elastic value representative of a level of elasticity is known, is disposed on a reference point (A, B) in a predetermined two-dimensional plane spreading within a subject, said method comprising the steps of:

detecting strains, $\epsilon_{xx}$ (x,y), $\epsilon_{xy}$ (x,y), $\epsilon_{yx}$ (x,y) and $\epsilon_{yy}$ (x,y) as to points (x, y) on an arbitrary route C in the two-demensional plane from a reference point (A, B) up to a predetermined observation point (X,Y), and their associated differential coefficients $\epsilon_{xx}$ (x,y), $_x$, $\epsilon_{xx}$ (x,y), $_y$, $\epsilon_{xy}$ (x,y), $_x$, $\epsilon_{xy}$ (x,y), $_y$, $\epsilon_{yy}$ (x,y), $_x$, $\epsilon_{yy}$ (x,y), $_y$;

detecting a curvilinear integral value on the route C from the reference point (A, B) up to the observation point (X,Y), the curvilinear integral value being given by the following expression; and $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)} \cdot$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\}_{,x}+\epsilon_{xy}(x,y)_{,y} \\ \epsilon_{yx}(x,y)_{,x}+\{\epsilon_{xx}(x,y)+2\epsilon_{yy}(x,y)\}_{,y} \end{pmatrix}$$

detecting an elastic value on the observation point (X, Y) on the basis of both the integral value and the elastic value of said reference member.

Also in the fifth and sixth elasticity measuring method as mentioned above, similar to the first to fourth elasticity measuring method, it is preferable that it is determined whether absolute values of the detonator of the integral kernel of said curvilinear integral, det={2$\epsilon_{xx}$ (x,y)+$\epsilon_{yy}$ (x,y)}·{$\epsilon_{xx}$ (x,y)+2 $\epsilon_{yy}$ (x,y)}−$\epsilon_{xy}$ (x,y)· $\epsilon_{yx}$ (x,y), with respect to the points (x, y) exceed a predetermined threshold, and if the absolute value of a detonator det={2$\epsilon_{xx}$ (x$_0$,y$_0$)+$\epsilon_{yy}$ (x$_0$,y$_o$)}·{$\epsilon_{xx}$ (x$_0$,y$_0$)+2 $\epsilon_{yy}$ ( x$_0$, y$_0$)}−$\epsilon_{xy}$ (x$_0$,y$_0$)·$\epsilon_{yx}$ (x$_0$,y$_0$) as to a predetermined point (x$_0$,y$_0$) of any of the points (x, y) is less than the threshold, the integral kernel as to the predetermined point (x$_0$,y$_0$) is replaced by a predetermined value to detect the integral value.

Still further, according to the present invention, there is provided the first elasticity measuring apparatus comprising:

(1) ultrasonic wave transmitting and receiving means for transmitting ultrasonic waves a plurality of number of times in the direction along a predetermined straight line extending inside of a subject and receiving the reflected ultrasonic waves to obtain an ultrasonic received signal;

(2) strain arithmetic means for detecting based on the ultrasonic received signal strains$\epsilon_{xx}$ (X) and $\epsilon_{xx}$ (A) of the subject as to an observation point X and a reference point A on the predetermined straight line, respectively, with respect to a direction toward which the straight line extends;

(3) ratio arithmetic means for detecting the ratio of the strains $\epsilon_{xx}$ (X) and $\epsilon_{xx}$ (A) to determine the ratio of elastic value-to-elastic value, which are representative of levels of elasticity involved in the observation point X and the reference point A, respectively; and (4) display means for displaying the ratio of elastic value-to-elastic value determined by said ratio arithmetic means.

Still further, according to the present invention, there is provided the second elasticity measuring apparatus comprising:

(1) strain arithmetic means for detecting, based on ultrasonic received signals each representative of a tomographic image measured at intervals of a specified time, which tomographic image is involved in a predetermined two-dimensional plane spreading within a subject, strains $\epsilon_{xx}$ (X) and $\epsilon_{xx}$ (A) of the subject as to an observation point X and a reference point A in the two-dimensional plane, respectively, with respect to a direction toward which a straight line coupling the observation point X and the reference point A extends;

(2) ratio arithmetic means for detecting the ratio of the strains $\epsilon_{xx}$ (X) and $\epsilon_{xx}$ (A) to determine the ratio of elastic value-to-elastic value, which are representative of levels of elasticity involved in the observation point X and the reference point A, respectively; and (3) display means for displaying the ratio of elastic value-to-elastic value determined by said ratio arithmetic means.

In the first and second elasticity measuring apparatus as mentioned above, it is preferable to provide such an arrangement that the elasticity measuring apparatus further comprises determining means for determining whether an absolute value of the strain $\epsilon_{xx}$ (X) on the observation point X exceeds a predetermined threshold, and said ratio arithmetic means outputs, if the absolute value is less than the threshold, a predetermined value by which the ratio of strain-to-strain respectively involved in said observation point X and said reference point A is replaced, instead of said ratio of strain-to-strain.

Still further, according to the present invention, there is provided the third elasticity measuring apparatus comprising:

(1) ultrasonic wave transmitting and receiving means for transmitting ultrasonic waves a plurality of number of times in the direction along a predetermined straight line extending inside of a subject and receiving the reflected ultrasonic waves to obtain an ultrasonic received signal;

(2) strain detecting means for detecting strain$\epsilon_{xx}$ (x) as to points on the straight line extending inside of the subject from the reference point A up to a predetermined observation point X, with respect to a direction toward which the straight line extends;

(3) differential coefficient arithmetic means for differentiating the strain$\epsilon_{xx}$ (x) in the direction toward which the straight line extends to detect a differential coefficient $\epsilon_{xx}$ (x), $_x$ of the strain $\epsilon_{xx}$ (x) with respect to the direction toward which the straight line extends;

(4) ratio arithmetic means for detecting an integral value of the ratio of the strain $\epsilon_{xx}$ (x) to the differential coefficient $\epsilon_{xx}$ (x), $_x$ along the straight line from the reference point A up to the observation point X, so that the ratio of elastic value-to-elastic value, which are representative of levels of elasticity involved in the reference point A and the observation point X, respectively, is detected; and (5) display means for displaying the ratio of elastic value-to-elastic value determined by said ratio arithmetic means.

Still further, according to the present invention, there is provided the fourth elasticity measuring apparatus comprising:

(1) strain detecting means for detecting, based on ultrasonic received signals each representative of a tomographic image measured at intervals of a specified time, which tomographic image is involved in a predetermined two-dimensional plane spreading within a subject, strain $\epsilon_{xx}$ (X) of the subject as to points on a straight line coupling a predetermined observation point X and a reference point A in the two-dimensional plane from the reference point A up to the observation point X, with respect to a direction toward which the straight line extends;

(2) differential coefficient arithmetic means for differentiating the strain$\epsilon_{xx}$ (x) in the direction toward which the straight line extends to detect a differential coefficient $\epsilon_{xx}$ (x), $\epsilon$ of the strain $\epsilon_{xx}$ (x) with respect to the direction toward which the straight line extends;

(3) ratio arithmetic means for detecting an integral value of the ratio of the strain $\epsilon_{xx}$ (x) to the differential coefficient$\epsilon_{xx}$(x),$_x$ along the straight line from the reference point A up to the observation point X, so that the ratio of elastic value-to-elastic value, which are representative of levels of elasticity-involved in the reference point A and the observation point X, respectively, is detected; and (4) display means for displaying the ratio of elastic value-to-elastic value determined by said ratio arithmetic means.

In the third and fourth elasticity measuring apparatus as mentioned above, it is preferable to provide such an arrangement that the elasticity measuring apparatus further comprises determining means for determining whether absolute values of the strain $\epsilon_{xx}$ (x) on the points x exceed a predetermined threshold, and if an absolute value of strain $\epsilon_{xx}$ ($x_0$) as to a predetermined point $x_0$ of any of the points x is less than the threshold, said ratio arithmetic means detects the integral value through replacing the ratio of the strain $\epsilon_{xx}$ ($x_0$) as to the predetermined point $x_0$ to the differential coefficient $\epsilon_{xx}$ ($x_0$),$_x$ by a predetermined value.

It is acceptable that the first to fourth elasticity measuring apparatus as mentioned above each further comprise:

(5) preset means for presetting an elastic value involved in the reference point A;

(6) elasticity arithmetic means for detecting an elastic value on the observation point X on the basis of both the ratio of elastic value-to-elastic value and the elastic value involved in the reference point A; and (7) additional display means for displaying the elastic value on the observation point X, instead of said display means.

Still further, according to the present invention, there is provided the fifth elasticity measuring apparatus comprising:

(1) ultrasonic wave transmitting and receiving means for transmitting ultrasonic waves a plurality of number of times in directions along a plurality of straight lines in a predetermined two-dimensional plane spreading within a subject and receiving the reflected ultrasonic waves to obtain ultrasonic received signals;

(2) strain detecting means for detecting strains, $\epsilon_{xx}$ (x,y), $\epsilon_{xy}$ (x,y), $\epsilon_{yx}$ (x,y) and $\epsilon_{yy}$ (x,y) as to points (x, y) on an arbitrary route C in a predetermined two-dimensional plane spreading within a subject from a reference point (A, B) up to a predetermined observation point (X,Y);

(3) differential coefficient arithmetic means for differentiating the strains, $\epsilon_{xx}$ (x,y), $\epsilon_{xy}$ (x,y), $\epsilon_{yx}$ (x,y) and $\epsilon_{yy}$ (x,y)

to detect their associated differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{xy}(x,y)_{,y}$;

(4) ratio arithmetic means for detecting a curvilinear integral value on the route C from the reference point (A,B) up to the observation point (X,Y), where the curvilinear integral value is given by the following expression $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)} \cdot$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\}_{,x}+\epsilon_{xy}(x,y)_{,y} \\ \epsilon_{yx}(x,y)_{,x}+\{\epsilon_{xx}(x,y)+2\epsilon_{yy}(x,y)\}_{,y} \end{pmatrix}$$

whereby the ratio of elastic value-to-elastic value, which are representative of levels of elasticity involved in the reference point (A, B) and the observation point (X, Y), respectively, is detected; and (5) display means for displaying the ratio of elastic value-to-elastic value determined by said ratio arithmetic means.

Still further, according to the present invention, there is provided the sixth elasticity measuring apparatus comprising:

(1) strain detecting means for detecting, based on ultrasonic received signals each representative of a tomographic image measured at intervals of a specified time, which tomographic image is involved in a predetermined two-dimensional plane spreading within a subject, strains, $\epsilon_{xx}(x,y)$, $\epsilon_{xy}(x,y)$, $\epsilon_{yx}(x,y)$, and $\epsilon_{yy}(x,y)$ as to points (x, y) on an arbitrary route C in a predetermined two-dimensional plane spreading within a subject from a reference point (A, B) up to a predetermined observation point (X,Y);

(2) differential coefficient arithmetic means for differentiating the strains, $\epsilon_{xx}(x,y)$, $\epsilon_{xy}(x,y)$, $\epsilon_{yx}(x,y)$ and $\epsilon_{yy}(x,y)$ to detect their associated differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{yy}(x,y)_{,y}$;

(3) ratio arithmetic means for detecting a curvilinear integral value on the route C from the reference point (A,B) up to the observation point (X,Y), where the curvilinear integral value is given by the following expression $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)} \cdot$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\}_{,x}+\epsilon_{xy}(x,y)_{,y} \\ \epsilon_{yx}(x,y)_{,x}+\{\epsilon_{xx}(x,y)+2\epsilon_{yy}(x,y)\}_{,y} \end{pmatrix}$$

whereby the ratio of elastic value-to-elastic value, which are representative of levels of elasticity involved in the reference point (A, B) and the observation point (X, Y), respectively, is detected; and (4) display means for displaying the ratio of elastic value-to-elastic value determined by said ratio arithmetic means.

In the fifth and sixth elasticity measuring apparatus as mentioned above, it is preferable to provide such an arrangement that the elasticity measuring apparatus further comprises determining means for determining whether absolute values of the detonator of the integral kernel of said curvilinear integral, det=$\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)$, with respect to the points (x, y) exceed a predetermined threshold, and if the absolute value of a detonator det=$\{2\epsilon_{xx}(x_0,y_0)+\epsilon_{yy}(x_0,y_0)\}\cdot\{\epsilon_{xx}(x_0,y_0)+2\epsilon_{yy}(x_0,y_0)\}-\epsilon_{xy}(x_0,y_0)\cdot\epsilon_{yx}(x_0,y_0)$ as to a predetermined point $(x_0,y_0)$ of any of the points (x, y) is less than the threshold, said ratio arithmetic means detects the integral value through replacing the integral kernel as to the predetermined point $(x_0,y_0)$ by a predetermined value.

It is acceptable that the fifth and sixth elasticity measuring apparatus as mentioned above each further comprise:

(6) preset means for presetting an elastic value involved in the reference point (A, B);

(7) elasticity arithmetic means for detecting an elastic value on the observation point (X, Y) on the basis of both the ratio of elastic value-to-elastic value and the elastic value involved in the reference point (A, B); and (8) additional display means for displaying the elastic value on the observation point (X, Y), wherein said display means is replaced by said additional display means.

According to the present invention as described above, it is possible to implement a quantitative measurement of elastic constants, which is hitherto considered that it is difficult to be attained without measuring a stress distribution, through only a measurement of distortion.

Hereinafter, a principle of the measurement of the elastic constant involved in the present invention will be described citing an example in which an elastic constant distribution of the tissue of a living body is measured.

Taking orthogonal coordinates axes as 1, 2 and 3, and assuming that a strain tensor is given by $$\begin{pmatrix} \epsilon_{11} & \epsilon_{12} & \epsilon_{13} \\ \epsilon_{21} & \epsilon_{22} & \epsilon_{23} \\ \epsilon_{31} & \epsilon_{32} & \epsilon_{33} \end{pmatrix}$$

and a stress tensor is given by $$\begin{pmatrix} \sigma_{11} & \sigma_{12} & \sigma_{13} \\ \sigma_{21} & \sigma_{22} & \sigma_{23} \\ \sigma_{31} & \sigma_{32} & \sigma_{33} \end{pmatrix}$$

The strain tensor $\epsilon_{ij}$ (i, j=1–3) can be determined in accordance with the following equation (1), depending on the respective elements $u_i$ (i, j=1–3) of the measured displacement vector.

$$\epsilon_{ij}=(u_{i,j}+u_{j,i})/2 \qquad (1)$$

where "$,j$" and "$,i$" imply the differential with respect to the j-direction and the differential with respect to the i-direction, respectively.

The strain tensor $\epsilon_{ij}$ (i, j=1–3) is expressed with the bulk strain $\epsilon_{aa}=\epsilon_{11}+\epsilon_{22}+\epsilon_{33}$ and the deviation strain $e_{ij}$ as follow:

$$\epsilon_{ij}=\epsilon_{aa}/3+e_{ij} \qquad (2)$$

and the stress tensor $\sigma_{ij}$ (i, j=1–3) is expressed with the means normal stress $p=\sigma_{aa}/3=(\sigma_{11}+\sigma_{22}+\sigma_{33})/3$ and the deviation stress $b_{ij}$ as follows:

$$\sigma_{ij}=p\delta_{ij}+b_{ij} \qquad (3)$$

where $\delta_{ij}$ is given by $$\delta_{ij} = \begin{cases} 1 & i=j \\ 0 & i \neq j \end{cases} \quad (4)$$

Thus, the strain and the stress have relation to each other through the bulk modulus K and the shear modulus G.

Specifically, the bulk modulus K and the shear modulus G are defined as the ratio of the means normal stress p to the bulk strain $\epsilon_{aa}$ and the ratio of the deviation stress $b_{ij}$ to the deviation strain $e_{ij}$, respectively.

$$p = K\epsilon_{aa} \quad (5)$$

$$b_{ij} = 2G\, e_{ij} \quad (6)$$

Since the tissue of a living body is regarded as an incompressible one, when Poisson ratio υ is given with 0.5, $$\epsilon_{aa} = 0 \quad (7)$$

substituting this for the related item in equation (2), $$\epsilon_{ij} = e_{ij} \quad (8)$$

and thus, $$K = 2G\,(1+\upsilon)/3\,(1-2\upsilon) = \infty \quad (9)$$

finally, the mean normal stress P is indeterminate in view of equation (5).

From equations (3), (6) and (8)

$$\sigma_{ij} = p\,\delta_{ij} 30\, 2G\, \epsilon_{ij} \quad (10)$$

It may be considered that an area within the tissue of a living body, for which the elastic constant distribution is intended to be detected, involves no mechanical source, and is independent of inertia because of a low frequency of movement. Thus, the following equilibrium equations exist.

$$\sigma_{11,1} + \sigma_{12,2} + \sigma_{13,3} = 0$$

$$\sigma_{21,1} + \sigma_{22,2} + \sigma_{23,3} = 0$$

$$\sigma_{31,1} + \sigma_{32,2} + \sigma_{33,3} = 0$$

The expression of the above equilibrium equations according to the sum rule is given by the following formula.

$$\sigma_{ij,j} = 0 \quad (11)$$

Next, the explanation will be made separately on different two cases (A) and (B).

(A) A case in which only a displacement on the primary axis (1-axis) with respect to the 1-axis direction can be measured, for example, such a case that by the use of a ultrasonic Doppler system, only a displacement on the points on ultrasound beams with respect to the ultrasound beam direction can be measured.

In such a case, since only the 1-axis direction is considered, it may be considered that there is no variation in medium with respect to the secondary axis (2-axis) direction and the tertiary axis direction. Thus, $$G_{,2} = G_{,3} = 0$$

Assuming that the expansion or compression as to the primary axis direction brings escape of the force in the secondary axis direction and the tertiary axis (3-axis) direction, $$\sigma_{12} = \sigma_{13} = \sigma_{23} = \sigma_{22}\sigma_{33} = 0 \quad (12)$$

$$\sigma_{21,1} = \sigma_{31,1} = \sigma_{ij,2} = \sigma_{ij,3} = 0 \quad (13)$$

From the equation (10), the stress $\sigma_{11}$ is given by $$\sigma_{11} = p + 2G\,\epsilon_{11} \quad (14)$$

On the other hand, the mean normal stress p is expressed, on the basis of the condition of equation (12), as follows.

$$p = \sigma_{aa}/3 = (\sigma_{11} + \sigma_{22} + \sigma_{33})/3 = \sigma_{11}/3 \quad (15)$$

Thus, equation (14) is expressed as follow;

$$\sigma_{11} = \sigma_{11}/3 + 2G\,\epsilon_{11} \quad (16)$$

and then $$\sigma_{11} = 3G\,\epsilon_{11} \quad (17)$$

In the differential of formula (17) in the primary axis direction, $$\sigma_{11,1} = 3)G_{,1}\epsilon_{11} + G\,\epsilon_{11,1}) \quad (18)$$

Formula (11) in the form of equilibrium equation means that the left side in the above-noted equation, $\sigma_{11,1}$, equals zero, that is, $\sigma_{11,1} = 0$ and thus, $$G_{,1}\epsilon_{11} + G\,\epsilon_{11,1} = 0$$

hence, $$G_{,1}/G = -\epsilon_{11,1}/\epsilon_{11} \quad (19)$$

Upon changing the notation of the coordinates axis from the primary axis, the secondary axis and the tertiary axis to the x-axis, the y-axis and the z-axis, respectively, now integrating both the sides of equation (19), $$\int_A^x G(x)_{,x}/G(x)dx = -\int_A^x \epsilon_{xx}(x)_{,x}/\epsilon_{xx}(x)dx \quad (20)$$

In the execution of the integral of the left part of equation (20), ln G(x)/G(A) is derived. The strain or strain $\epsilon_{xx}(x)$ is equivalent to one which is obtained through differentiating x-component $u_x(x)$ of the displacement vector with respect to x.

$$\therefore \ln\{G(x)/G(A)\} = -\int_A^x [u_x(x)_{,x}]_{,x}/u_x(x)_{,x}dx \quad (21)$$

In a case where a zero-point exists with respect to the item $u_x(x)_{,xx}$, it will be possible to avoid the problems by means of adopting such a scheme that the item $[u_x(x)_{,x}]_{,x}/u_x(x)_{,x}$ is given by zero, alternatively, such item is replaced by the value $[u_x(x+dx)_{,x}]_{,x}/u_x(x+dx)$ involved in the neighboring point (x+dx).

Equation (21) may be rewritten as follows:

$$\begin{aligned}\ln\{G(x)/G(A)\} &= -\ln\{\epsilon_{xx}(x)/\epsilon_{xx}(A)\} \\ &= \ln\{\epsilon_{xx}(A)/\epsilon_{xx}(x)\} \\ &= \ln\{u_x(A)_{,x}/u_x(x)_{,x}\}\end{aligned} \quad (22)$$

Accordingly, it will be understood that the following expression is also applicable to the determination.

$$\begin{aligned}G(x)/G(A) &= \epsilon_{xx}(A)/\epsilon_{xx}(x) \\ &= u_x(A)_{,x}/u_x(x)_{,x}\end{aligned} \quad (23)$$

Further, it is possible to detect an absolute shear modulus by means of putting on the point A the material of which the shear modulus is known. Assuming that the shear modulus of such a material is given with $G_0$, it is possible to determine the logarithm of the shear modulus, or the shear modulus in the form of the following expressions:

$$\ln G(x) = \ln\{G(x)/G(A)\} + \ln G_0 \quad (24)$$
$$= -\int_A^x [u_x(x)_{,x}]_{,x}/u_x(x)_{,x} dx + \ln G_0$$

or, $$G(x) = G(x)/G(A) \cdot G_0 \quad (25)$$
$$= \epsilon_{xx}(A)/\epsilon_{xx}(x) \cdot G_0$$

The above explanation concerns a principle of the measurement of the elastic constant involved in the first to fourth elasticity measuring method, and the first to fourth elasticity measuring apparatus according to the present invention.

(B) A case in which two-way components of a displacement vector on the points in a two-dimensional plane can be measured, for example, such a case that the use of a two-dimensional cross-correlation for a two-dimensional small area permits the detection of a displacement with respect to the ultrasound beam direction and an additional displacement with respect to the direction which falls at right angles with the ultrasound beam direction.

In such a case, the shear modulus G distributes in a plane (1, 2) when taking orthogonal coordinates axes as 1, 2 and 3, and there is no variation with respect to the 3-axis direction. Thus, $$G_{,3}=0$$

Effect from the exterior merely causes the expansion or compression to emanate within the plane (1, 2), and the force escapes in the 3-axis direction, that is, $$\sigma_{13}=\sigma_{23}=\sigma_{33}=0 \quad (26)$$

$$\sigma_{31,1}=\sigma_{32,2}=\sigma_{ij,3}=0 \quad (27)$$

From the equation (10), the stress $\sigma_{11}, \sigma_{22}, \sigma_{12}, \sigma_{21}$ are given by $$\sigma_{11}=p+2G\,\epsilon_{11} \quad (28)$$

$$\sigma_{22}=p+2G\,\epsilon_{22} \quad (29)$$

$$\sigma_{12}=2G\,\epsilon_{12} \quad (30)$$

$$\sigma_{21}=2G\,\epsilon_{21} \quad (31)$$

On the other hand, mean normal stress p is expressed, on the basis of the condition of equation (20), as follows.

$$p=\sigma_{aa}/3=(\sigma_{11}+\sigma_{22}+\sigma_{33})/3=(\sigma_{11}+\sigma_{22})/3 \quad (32)$$

Thus, substituting equations (28) and (29) for equation (32), $$p=(p+2G\epsilon_{11}+p+2G\epsilon_{22})/3$$

$$3p=2p+2G(\epsilon_{11}+\epsilon_{22})$$

$$\therefore p2G(\epsilon_{11}+\epsilon_{22}) \quad (33)$$

substituting the above equation for equations (28) and (29), $$\sigma_{11}=2G(2\,\epsilon_{11}+\epsilon_{22}) \quad (34)$$

$$\sigma_{22}=2G(\epsilon_{11}+2\,\epsilon_{22}) \quad (35)$$

In the differential of formulas (34), (30), (31) and (35) in the 1-axis direction or the 2-axis direction, $$\sigma_{11,1}=2(G_{,1}(2\epsilon_{11}+\epsilon_{22})+G(2\epsilon_{11}+\epsilon_{22})_{,1}) \quad (36)$$

$$\sigma_{12,2}=2(G_{,2}\,\epsilon_{12}+G\,\epsilon_{12,2}) \quad (37)$$

$$\sigma_{21,1}=2)G_{,1}\,\epsilon_{21}+G\,\epsilon_{21,1}) \quad (38)$$

$$\sigma_{22,2}=2(G_{,2}(\epsilon_{11}+2\,\epsilon_{22})+G(\epsilon_{11}+2\,\epsilon_{22})_{,2}) \quad (39)$$

From equilibrium equation (11) and (27), $$\sigma_{11,1}+\sigma_{12,2}=0$$

$$\sigma_{21,1}+\sigma_{22,2}=0$$

and thus, $$\begin{pmatrix} 2\epsilon_{11}+\epsilon_{22} & \epsilon_{12} \\ \epsilon_{21} & \epsilon_{11}+2\epsilon_{22} \end{pmatrix} \begin{pmatrix} G_{,1}/G \\ G_{,2}/G \end{pmatrix} = \quad (40)$$

$$-\begin{pmatrix} (2\epsilon_{11}+\epsilon_{22})_{,1}+\epsilon_{12,2} \\ \epsilon_{21,1}+(\epsilon_{11}+2\epsilon_{22})_{,2} \end{pmatrix}$$

Formula (40) can be solved as to an area in which determinant, that is, the following det is not zero:

$$\det = (2\epsilon_{11}+\epsilon_{22})(\epsilon_{11}+2\epsilon_{22})-\epsilon_{12}\epsilon_{21}$$
$$= (2\epsilon_{11}+\epsilon_{22})(\epsilon_{11}+2\epsilon_{22})-\epsilon_{12}^2$$

and the gradient $\nabla (\ln G)$ is determined in accordance with the following formula:

$$\nabla(\ln G) = \begin{pmatrix} G_{,1}/G \\ G_{,2}/G \end{pmatrix} = -\frac{1}{\det} \begin{pmatrix} \epsilon_{11}+2\epsilon_{22} & -\epsilon_{12} \\ -\epsilon_{21} & 2\epsilon_{11}+\epsilon_{22} \end{pmatrix} \cdot \quad (41)$$

$$\begin{pmatrix} (2\epsilon_{11}+\epsilon_{22})_{,1}+\epsilon_{12,2} \\ \epsilon_{21,1}+(\epsilon_{11}+2\epsilon_{22})_{,2} \end{pmatrix}$$

Upon changing the notation of the coordinates axis from the 1-axis, the 2-axis and the 3-axis to the x-axis, the y-axis and the z-axis, respectively, when conducting the curvilinear integral with respect to an arbitrary route C, the relative shear modulus with respect to the reference point (A, B) is determined in accordance with the following formula:

$$\ln\{G(x,y)/G(A,B)\} = \int_c \nabla(\ln G(x,y)) \cdot ds = \quad (42)$$

$$\int_c \left( \frac{\partial}{\partial x} \ln G(x,y) dx + \frac{\partial}{\partial y} \ln G(x,y) dy \right) =$$

$$\int_c \left( \frac{G(x,y)_{,x}}{G(x,y)} dx + \frac{G(x,y)_{,y}}{G(x,y)} dy \right) =$$

$$-\int_c \frac{1}{\det} \cdot (dx\ dy) \cdot$$

$$\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix} \cdot$$

$$\begin{pmatrix} (2\epsilon_{xx}(x,y)+\epsilon_{yy}(x,y))_{,x}+\epsilon_{xy}(x,y)_{,y} \\ \epsilon_{yx}(x,y)_{,x}+(\epsilon_{xx}(x,y)+2\epsilon_{yy}(x,y))_{,y} \end{pmatrix}$$

It is preferable that the route C of the integral is selected in such a manner that the determinant does not become zero. If it is difficult in structure of the system to avoid the point on which the determinant becomes zero, it will be possible to avoid the problems by means of adopting such a scheme that the item $\nabla (\ln G(x,y))$ is given by zero, alternatively, such item is replaced by the value involved in the neighboring point.

Further, it is also possible, on a similar basis as discussed above, to detect an absolute shear modulus by means of putting on the point (A, B) the material of which the shear modulus is known. When the curvilinear integral value in formula (42) is given with S, formula (42) is denoted as follows;

$$\ln G(x, y) = S + \ln G(A, B)$$

and when G (A, B) is given with the known shear modulus $G_0$, the above equation is rewritten as follows:

$$\ln G(x, y) = S + \ln G_0 \tag{43}$$

The above explanation concerns a principle of the measurement of the elastic constant involved in the fifth and sixth elasticity measuring method, and the fifth and sixth elasticity measuring apparatus according to the present invention.

While both the above-described cases (A) and (B) are each to detect the shear modulus G, Young's modulus E is expressed with the shear modulus G and Poisson ratio $\upsilon$ as follows:

$$E = 2(1+\upsilon) G \tag{44}$$

and Poisson ratio is regarded as 0.5. Hence, $$E = 3G \tag{45}$$

Accordingly, it is possible to present information in the form of Young's modulus E. Further, it is noted that the present invention does not always require to detect or measure the strictly defined elastic constant, such as the shear modulus G, Young's modulus E and the like, and it is acceptable to detect, for example, the logarithm in G of the shear modulus, and the like, as mentioned above.

BRIEF DESCRIPTION OF THE DRAWINGS

FIG. 3 is a view showing a step by which the step (1_4) in the flowchart of FIG. 1 can be replaced;

FIG. 5 is a view showing a step by which the step (4_5) in the flowchart of FIG. 4 can be replaced;

FIG. 6 is a view showing a step by which the step (4_6) in the flowchart of FIG. 4 can be replaced, in a case where material having a known shear modulus $G_0$ is put on a point A;

FIG. 22A is a block diagram showing an integrator by way of example in a case where an analog signal is dealt with;

FIG. 23A is a block diagram showing an integrator by way of example in a case where a digital signal is dealt with;

DESCRIPTION OF THE PREFERRED EMBODIMENTS

Hereinafter, there will be described embodiments of the present invention.

Figure 1:
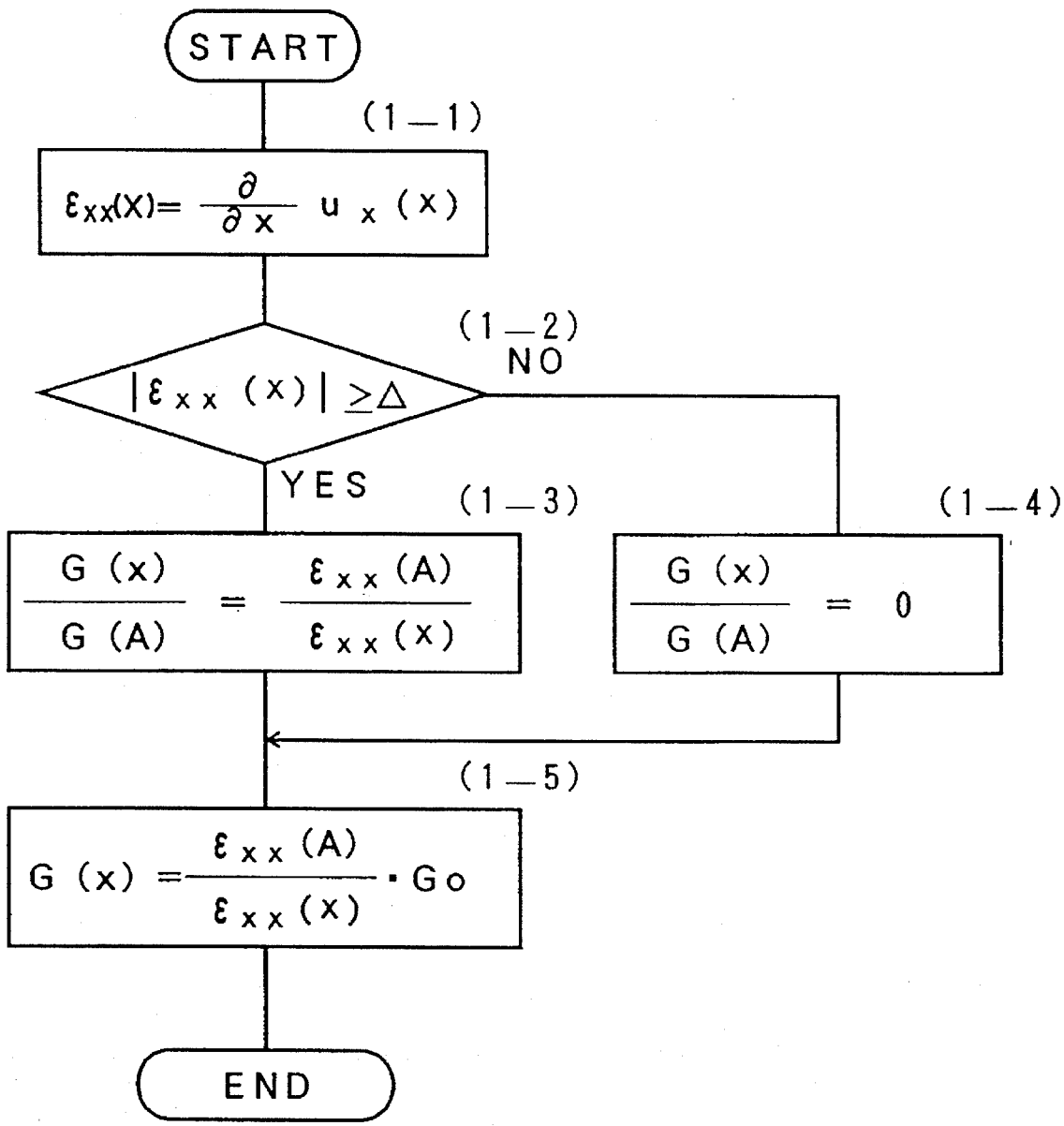
FIG. 1 is a flowchart useful for understanding an elasticity measuring method according to the first embodiment concerning a method of the present invention.

FIG. 1 is a flowchart useful for understanding an elasticity measuring method according to the first embodiment concerning a method of the present invention. FIGS. 2 (A)–(D) are each a view showing the function in the flowchart of FIG. 1 by way of example.

Figure 2A:
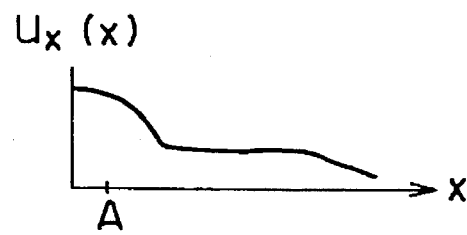
FIGS. 2 (A)–(D) are each a view showing the function in the flowchart of FIG. 1 by way of example.
Figure 2B:
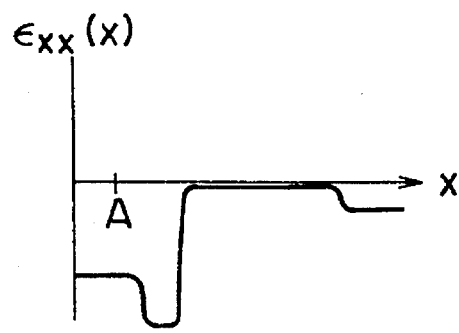
Figure 2C:
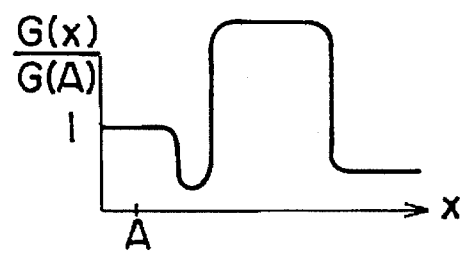

Now, prior to practicing the present embodiment shown in FIG. 1, there is determined displacement $U_x$ (x) on the respective points on a predetermined straight line (an x-direction) extending in the subject, for example, as shown in FIG. 2(A). The displacement $U_x$ (x) may be measured, irrespective of a way of determination, by the use of, for example, a so-called ultrasonic diagnostic system in which ultrasonic acoustic waves are transmitted into the subject, and upon receipt of the reflected ultrasonic acoustic waves, images involved in the inside of the subject are obtained; a X-ray CT (computed tomography) in which X-rays are irradiated to the subject to derive tomographic images of the inside of the subject; or an MRI (magnetic resonance imaging) in which tomographic images of the inside of the subject are derived utilizing the nuclear magnetic resonance.

In step (1_1) shown in FIG. 1, displacement $U_x$ (x) is differentiated with respect to the x-direction to determine strain $\epsilon_{xx}$ (x) involved in the x-direction. The strain $\epsilon_{xx}$ (x) is shown, for example, in FIG. 2(B). In step (1_2), the absolute value $|\epsilon_{xx}$ (x)$|$ of the determined strain $\epsilon_{xx}$ (x) is compared with a threshold $\Delta$. If the absolute value $|\epsilon_{xx}$ (x)$|\geq\Delta$, the process goes to the step (1_3) in which the ratio of the shear modulus G(x) at the observation point x to the shear modulus G(A) at the reference point A are determined in accordance with the aforementioned equation (23) (refer to FIG. 2(C)).

If the absolute value $|\epsilon_{xx}$ (x)$|<\Delta$, the process goes to the step (1_4) in which there is given G(x)/G(A)=0, since the performance of the arithmetic operation according to the step (1_3) will give too large value for G(x)/G(A) to expect accuracy.

Figure 2D:
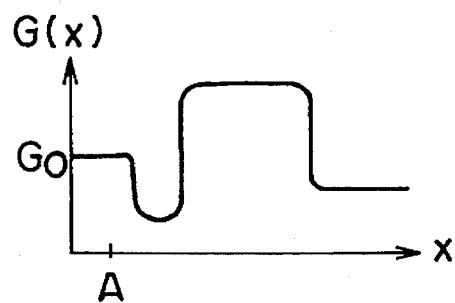

In the step (1_5), assuming that the shear modulus G(A) at the reference point A is given by the known value $G_0$, the shear modulus G(x) at the observation point x is calculated (refer to FIG. 2(D)).

Incidentally, for example, in a case where an elastic constant distribution of the tissue of a living body is detected to be available for the diagnosis, it is sufficient that a relative elastic constant such that to what extent a portion deemed be the lesion is hardened in comparison with its periphery is seen, and it often happens that there is no need to detect the elastic constant itself. In such a case, the step (1_5) shown in FIG. 1 is not needed.

Further, according to the present embodiment, there is shown an example such that first, displacement $U_x$ (x) is determined, and the displacement $U_x$ (x) is differentiated with respect to the x-direction to determine the strain $\epsilon_{xx}$ (x) involved in the x-direction. However, the present invention is not restricted to such an example. For example, there is known a photoelasticity method such that a strain distribution of a transparent body such as glass, celluloid and the like is determined by utilizing of the phenomenon that when such a transparent body is strained, a polarization state of the light passing through the transparent body is varied. The present invention does not exclude such a modification that the strain $\epsilon_{xx}$ (x) is directly determined, without determining the displacement $U_x$ (x), by the use of the technique as mentioned above. Further, it is noted that as shown in another embodiment, which will be described later, there is a technique of directly determining the strain on the basis of a signal carrying internal information of the subject, such as an ultrasonic received signal and the like.

Figure 3:
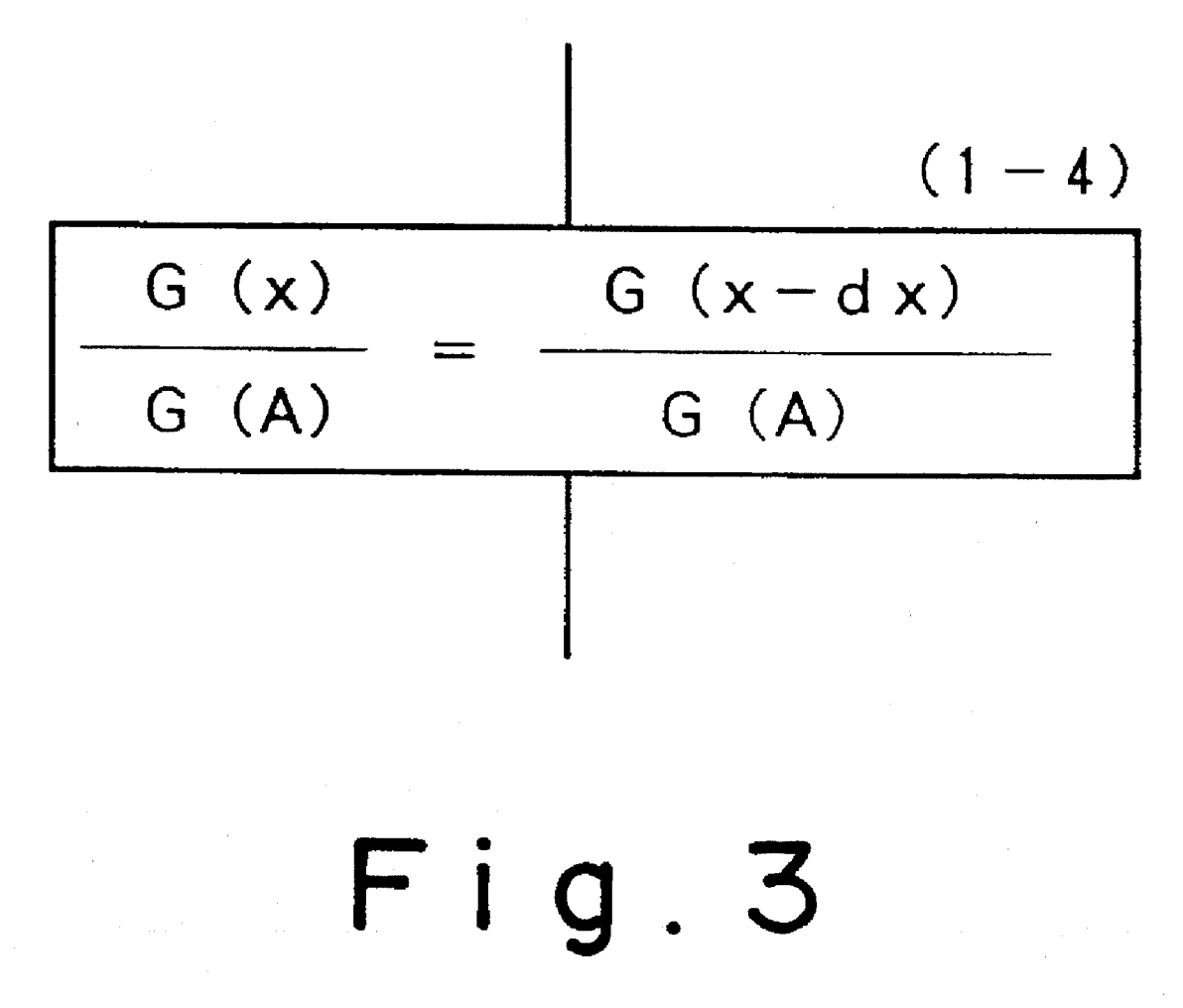

FIG. 3 is a view showing a step by which the step (1_4) in the flowchart of FIG. 1 can be replaced.

In the step (1_2), if $|\epsilon_{xx}(x)|<\Delta$, it is acceptable to replace the equation G(x)/G(A)=0 by the equation G(x)/G(A)=G(x−dx)/G(A), where G(x−dx) is the shear modulus at the point (x−dx) near the observation point x.

Incidentally, according to the present invention, the step (1_2) shown in FIG. 1 does not necessarily have to be provided. It is acceptable to arrange the system in such a way that an arithmetic operation according to the step (1_3) is executed omitting the step (1_2). For example, in a case where it is expected that the strain $\epsilon_{xx}$ (x) always exceeds the threshold $\Delta$, that is, $|\epsilon_{xx}$ (x)$|\geq\Delta$, the step (1_2) is not of course needed. On the other hand, even if there is expected the possibility of $|\epsilon_{xx}$ (x)$|<\Delta$, the extremely large value of G(x) detected may be neglected. But, with respect to $\epsilon_{xx}$ (x)=0 itself, it is preferable to avoid this term, since the execution of the division in the step (1_3) becomes impossible.

Figure 4:
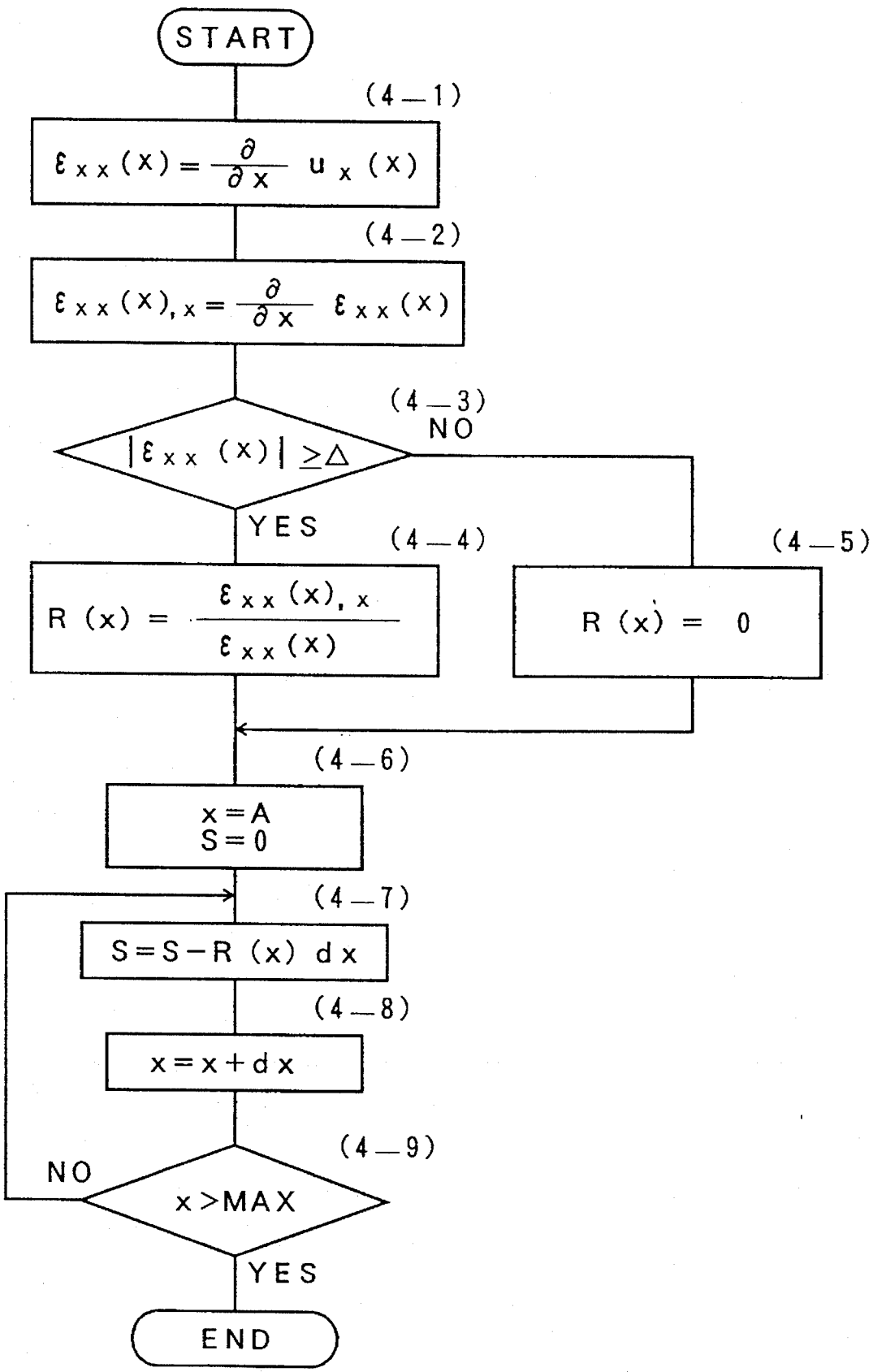
FIG. 4 is a flowchart useful for understanding an elasticity measuring method according to the second embodiment concerning a method of the present invention.

FIG. 4 is a flowchart useful for understanding an elasticity measuring method according to the second embodiment concerning a method of the present invention;

In step (4_1) shown in FIG. 4, displacement $U_x$ (x) of the subject on a predetermined straight line extending toward inside of the subject in the x-direction which the straight line extends in is differentiated with respect to the x-direction to determine strain $\epsilon_{xx}$ (x) involved in the x-direction. In step (4_2), the strain $\epsilon_{xx}$ (x) is differentiated with respect to the x-direction to determine a differential coefficient $\epsilon_{xx}$ (x), $_x$ of the strain $\epsilon_{xx}$ (x).

In step (4_3), the absolute value $|\epsilon_{xx}$ (x)$|$ of the determined strain $\epsilon_{xx}$ (x) is compared with a threshold $\Delta$. If the absolute value $|\epsilon_{xx}$ (x)$|\geq\Delta$, the process goes to the step(4_4) in which the following formula is calculated.

$$R(x) = \epsilon_{xx}(x),_x/\epsilon_{xx}(x)$$

If the absolute value $|\epsilon_{xx}$ (x)$|<\Delta$, the process goes to the step (4_5) in which there is given $$R(x)=0$$

In step (4_6), the initialization is conducted so as to provide x=A, and S=0. In step (4_7), the following formula is calculated:

$$S=S-R(x)\cdot\Delta x \cdot dx$$

where $\Delta x$ is a sampling interval in the x-direction and dx=1 or 0 or −1. In step (4_8), the value x is increased by the infinitely small increment dx. In step (4_9), it is determined whether or not the value x has reached the maximum value MAX. The steps (4_7), (4_8) and (4_9) are repeated until the condition x>MAX is satisfied.

This is to determine logarithm of the ratio of the shear modulus G(x) at the point x to the shear modulus G(A) at the point A in accordance with the aforementioned equation (21), that is, $$S=\ln\{G(x)/G(A)\}$$

Figures 5, 6:
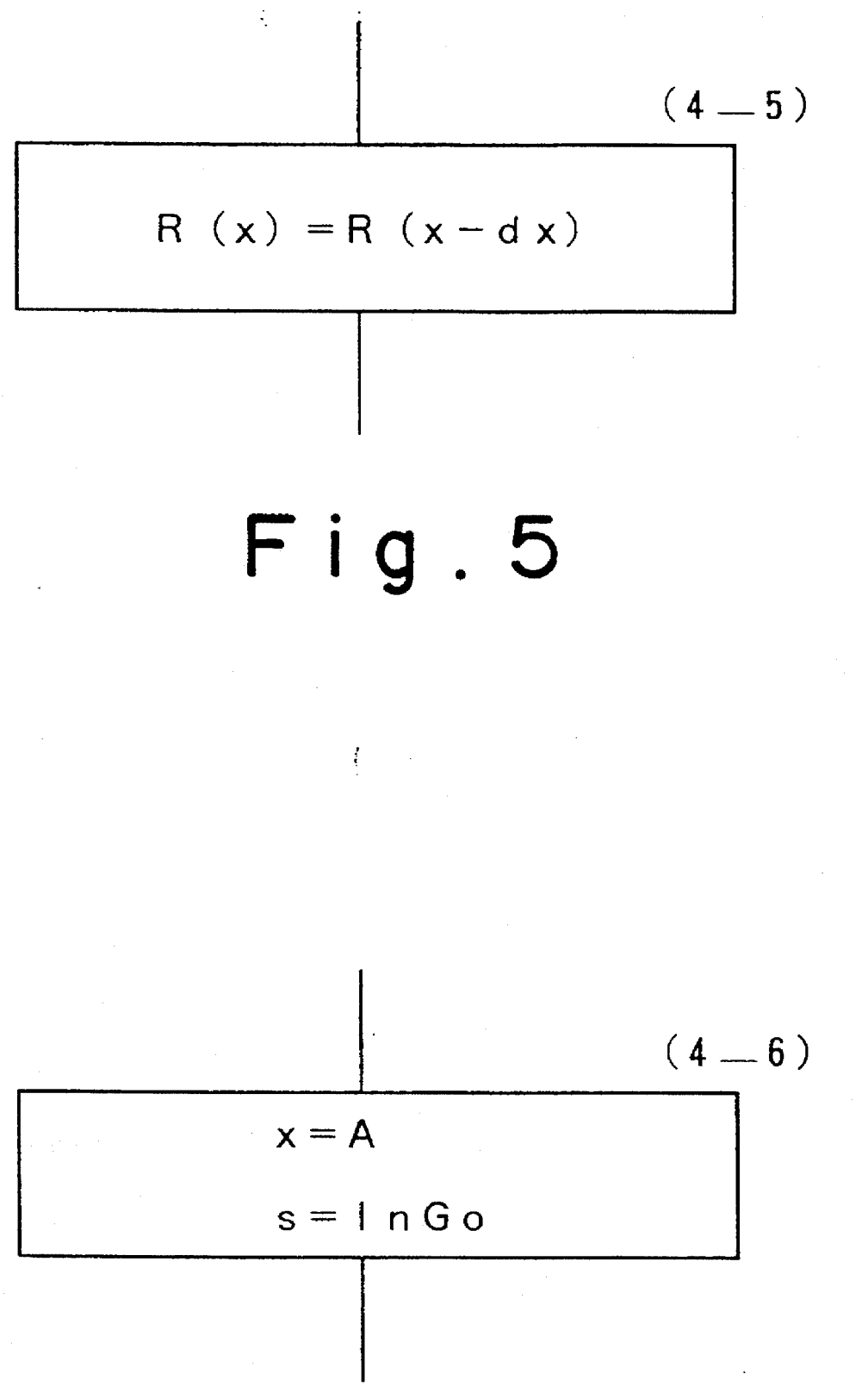

FIG. 5 is a view showing a step by which the step (4_5) in the flowchart of FIG. 4 can be replaced. In this step, when $|\epsilon_{xx}(x)|<\Delta$, R(x) is replaced by R(x−dx) which is involved in the value near the point x.

FIG. 6 is a view showing a step by which the step (4_6) in the flowchart of FIG. 4 can be replaced, in a case where material having a known shear modulus $G_0$ is put on a point A. In this step, when the initial value for S is given by $S=\ln G_0$, the logarithm of the shear modulus G(x) at the point x, that is, $S=\ln G(x)$ can be calculated.

Figure 7:
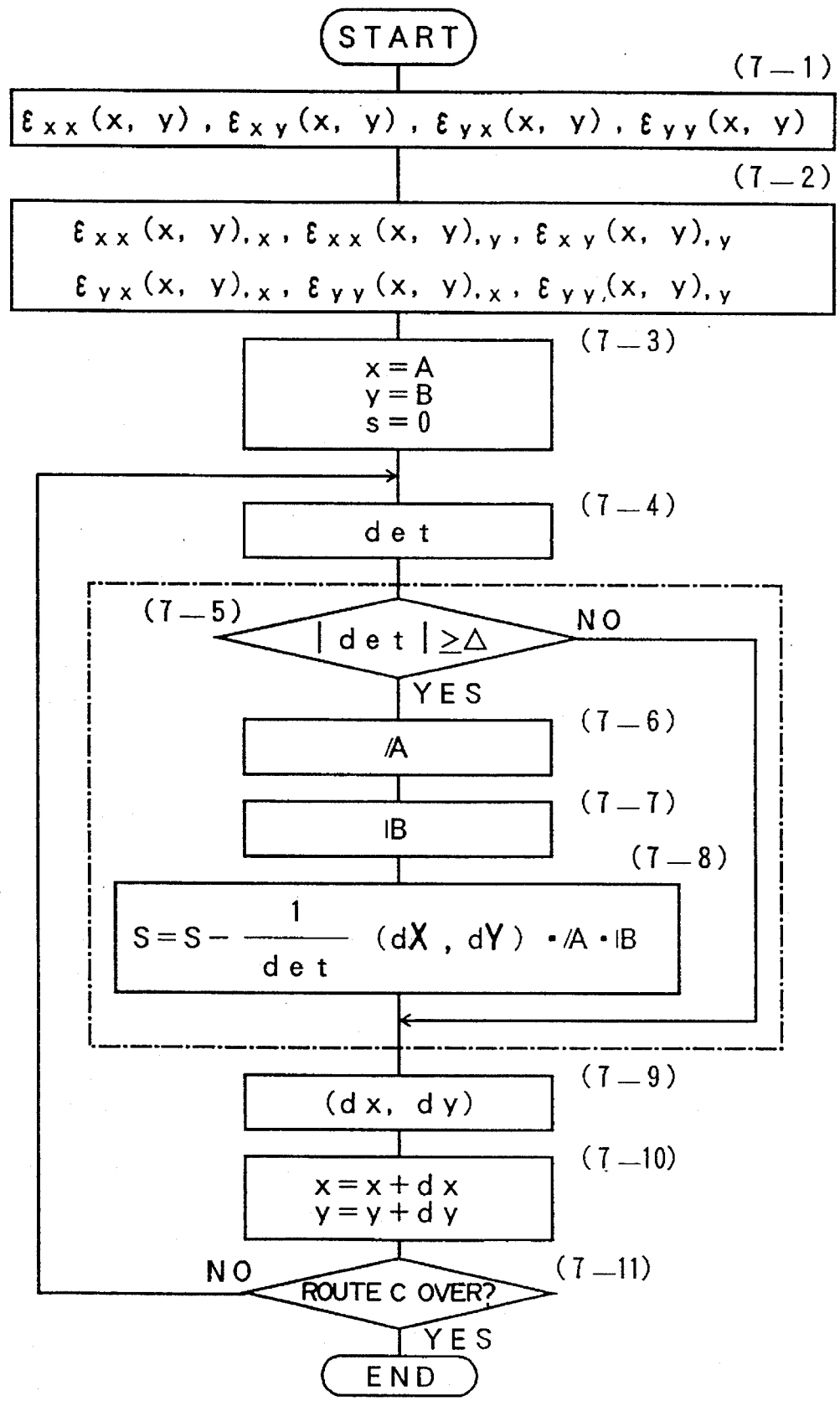
FIG. 7 is a flowchart useful for understanding an elasticity measuring method according to the third embodiment concerning a method of the present invention.

FIG. 7 is a flowchart useful for understanding an elasticity measuring method according to the third embodiment concerning a method of the present invention. This embodiment shows an example in which displacement distributions $U_x(x, y)$ and $U_y(x, y)$ in a predetermined two dimensional plane spreading inside of the subject are determined. This is to determine logarithm of the ratio of the shear modulus G(x, y) at the point (x, y) to the shear modulus G(A, B) at the point (A, B) in accordance with the aforementioned equation (42), that is, ln {(G(x,y)/G(A,B)}.

In step (7_1), first, strain distributions are determined in accordance with the arithmetic expressions as set forth below:

$$\epsilon_{xx}(x, y)=(\delta/\delta x) u_x(x, y)$$

$$\epsilon_{yy}(x, y)=(\delta/\delta y) u_y(x, y)$$

$$\epsilon_{xy}(x, y)=\epsilon_{yx}(x, y)=\tfrac{1}{2}\{(\delta/\delta x) u_y(x, y)+ (\delta/\delta y) u_x(x, y)\}$$

In step (7_2), the strain distributions obtained in the step (7_1) are further differentiated so that differential coefficients of the strain are determined. The equations are given by $$\epsilon_{xx}(x,y)_{,x}=(\delta/\delta x)\,\epsilon_{xx}(x,y)$$

$$\epsilon_{xx}(x,y)_{,y}=(\delta/\delta y)\,\epsilon_{xx}(x,y)$$

$$\epsilon_{yy}(x,y)_{,x}=(\delta/\delta x)\,\epsilon_{yy}(x,y)$$

$$\epsilon_{yy}(x,y)_{,y}=(\delta/\delta y)\,\epsilon_{yy}(x,y)$$

$$\epsilon_{xy}(x,y)_{,y}=(\delta/\delta y)\,\epsilon_{xy}(x,y)$$

$$\epsilon_{yx}(x,y)_{,x}=(\delta/\delta x)\,\epsilon_{yx}(x,y)$$

In step (7_3), the initialization is effected to provide x=A, and y=B so that a reference point (A, B) is designated, and in addition to provide S=0.

In step (7_4), the following arithmetic operation is carried out:

$$\det=\{2\epsilon_{xx}(x,y)+\epsilon_{yy}(x,y)\}\cdot\{\epsilon_{xx}(x,y)+ 2\epsilon_{yy}(x,y)\}-\epsilon_{xy}(,x,y)\cdot\epsilon_{yx}(x,y)$$

where "det" corresponds to a denominator of the integral kernel in the aforementioned equation (42).

In step (7_5), the determination as to $|\det|\geq\Delta$ is conducted for the purpose of avoiding such a situation that the integral kernel in the equation (42) becomes extremely large.

In steps (7_6) and (7_7), the following values are determined, respectively.

$$A=\begin{pmatrix} \epsilon_{xx}(x,y) + 2\epsilon_{yy}(x,y) & -\epsilon_{xy}(x,y) \\ -\epsilon_{yx}(x,y) & 2\epsilon_{xx}(x,y) + \epsilon_{yy}(x,y) \end{pmatrix}$$

$$B=\begin{pmatrix} (2\epsilon_{xx}(x,y) + \epsilon_{yy}(x,y))_{,x} + \epsilon_{xy}(x,y)_{,y} \\ \epsilon_{yx}(x,y)_{,x} + (\epsilon_{xx}(x,y) + 2\epsilon_{yy}(x,y))_{,y} \end{pmatrix}$$

In step (7_8), arithmetic operation according to the following formula is carried out.

$$S=S-(1/\det)(dX\ dY)\cdot A\cdot B$$

wherein $dX=\Delta x\, dx$, $dY=\Delta y\, dy$, and $\Delta x$ and $\Delta y$ are sampling units.

In step (7_9), infinitely small increments, dx and dy, are determined in such a manner that the infinitely small increment vector (dx, dy) is orientated toward the tangential direction of a predetermined route C.

Figure 8:
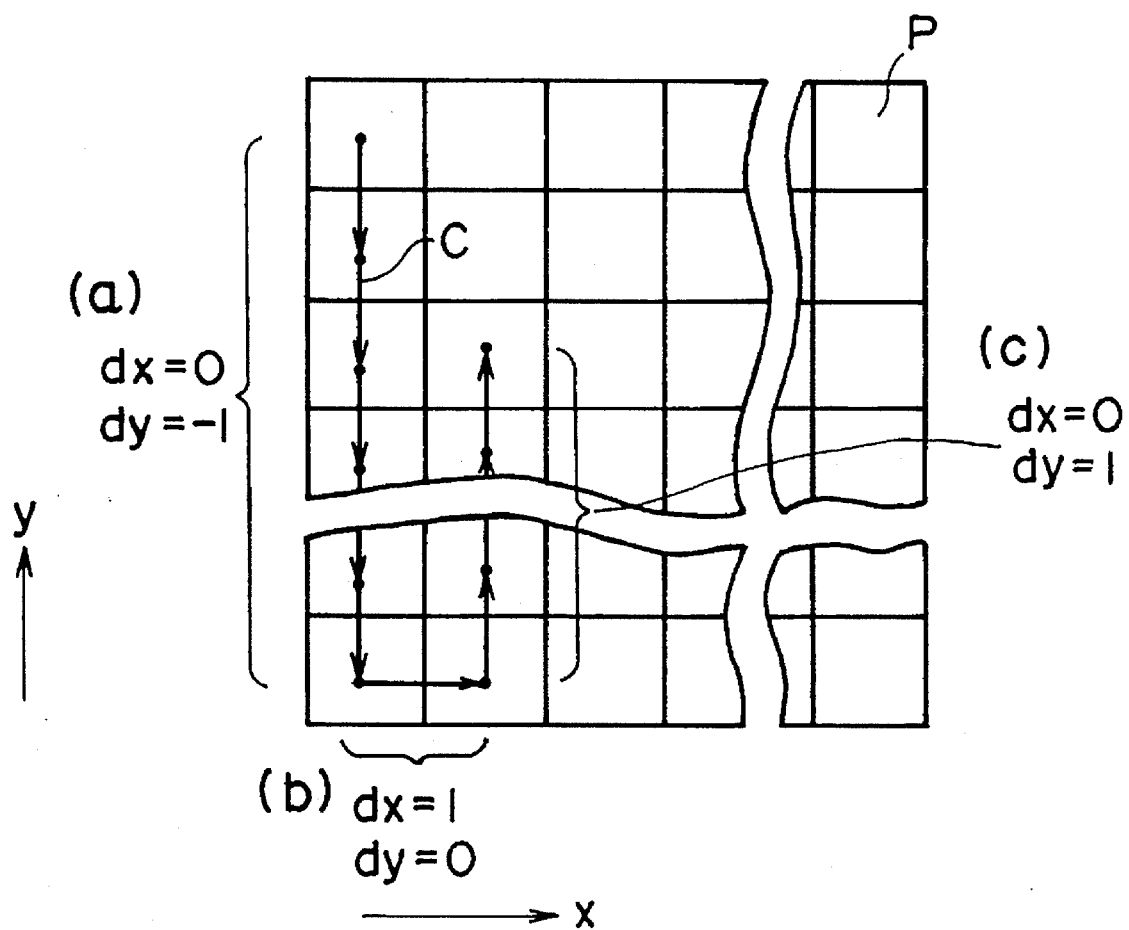
FIG. 8 is a typical illustration useful for understanding how infinitely small increments, dx and dy are determined.

FIG. 8 is a typical illustration useful for understanding how infinitely small increments, dx and dy, are determined.

In case of advancement along the route C on the two dimensional plane C, there are given dx=0, dy=−1 for the section (a), dx=1, dy=0 for the section (b), and dx=0, dy=1 for the section (c).

Incidentally, if the route C is determined previously, it is possible to calculate beforehand also the infinitely small increments (dx, dy) along the route C. Thus, it is acceptable to store the previously calculated (dx dy) in a ROM or the like.

Now, again referring to FIG. 7, when the infinitely small increments (dx, dy) is given in step (7_9), in step (7_10), x and y are increased by infinitely small increments (dx, dy), respectively. In step (7_9), it is determined as to whether or not the process advances up to the final course of the route C, and if not yet, the program returns to step (7_4). Thus, through the arithmetic operation, the equation (42) is executed so that the values on point (x, y) along the route C is obtained according to the following formula.

$$S=\ln\{G)x,y)/G(A,B)\}$$

In step (7_5), if it is determined as $|\det|<\Delta$, the process goes to the step (7_9), without calculating the new S in the step (7_8). This means that in case of $|\det|<\Delta$, as the value S (x, y) of S of the point (x, y), the value S (x−dx, y−dy) of S of the just prior point (x−dx, y−dy) is used as it is, in other words, the integral kernel of the equation (42) is replaced by zero with respect to the point (x, y).

Figure 9:
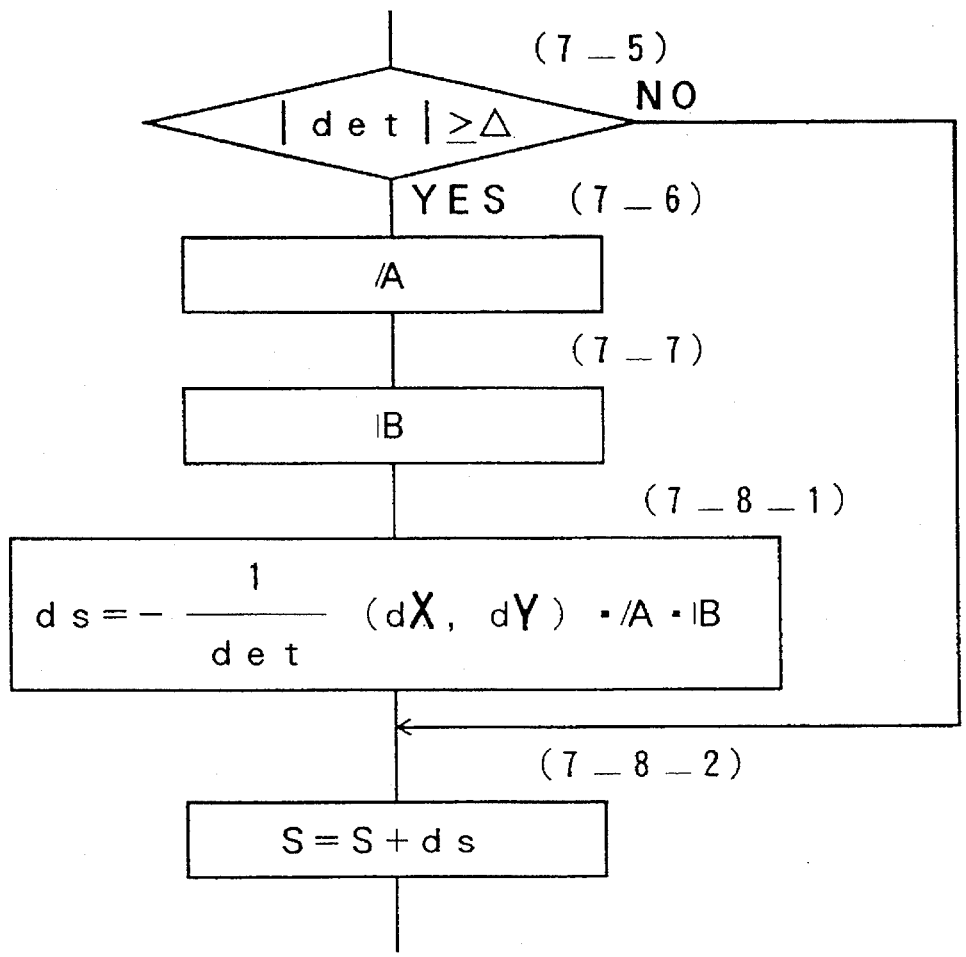
FIG. 9 is a view showing steps by which the steps (7_5) to (7_8) circled with a dashed line in the flowchart of FIG. 7 can be replaced.

FIG. 9 is a view showing steps by which the steps (7_5) to (7_8) circled with a dashed line in the flowchart of FIG. 7 can be replaced.

The difference of the replaced portion from the associated portion of FIG. 7 resides in the point that there are provided two steps (7_8_1) and (7_8_2) instead of the step (7_8) of FIG. 7, and in the step (7_5) when it is decided as $|\det|<\Delta$, then, directly, the step (7_8_2) is executed.

In FIG. 9, it is noted that when $|\det|<\Delta$, as the integral kernel of the point (x, y) on which the current arithmetic operation is performed, the integral kernel of the immediately prior point (x−dx, y−dy) is used as it is, so that S is determined. In this manner, according to the embodiment shown in FIG. 9, when $|\det|<\Delta$, the integral kernel of the neighboring point (x−dx, y−dy) is used as it is.

Figure 10:
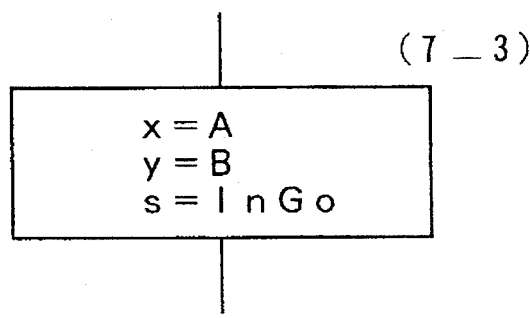
FIG. 10 is a view showing a step by which the step (7_3) in the flowchart of FIG. 7 can be replaced, in a case where material having a known shear modulus $G_0$ is put on a point (A, B)
Figure 11:
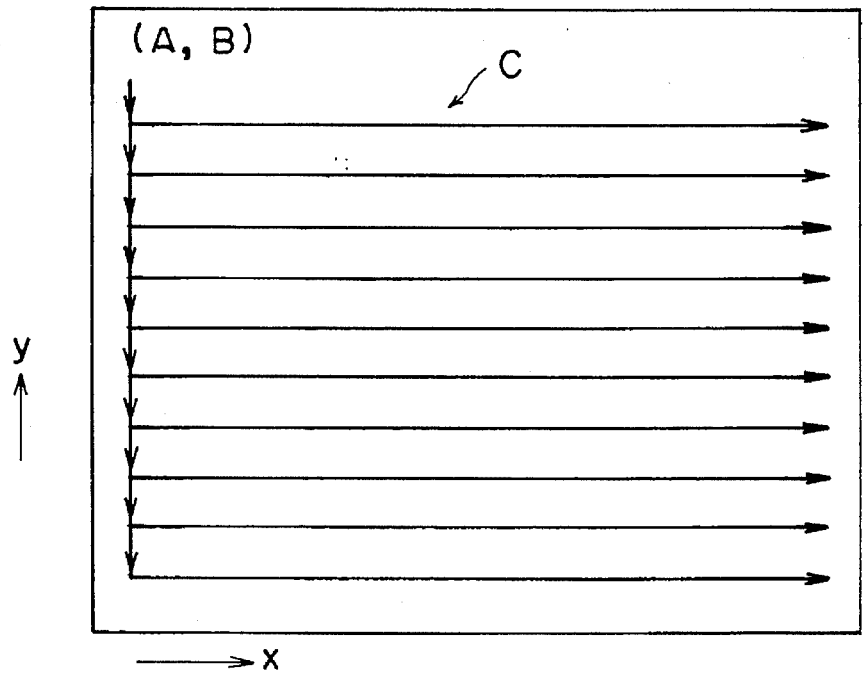
FIG. 11 is a view showing exemplarily a route C starting from a point (A, B)
Figure 12:
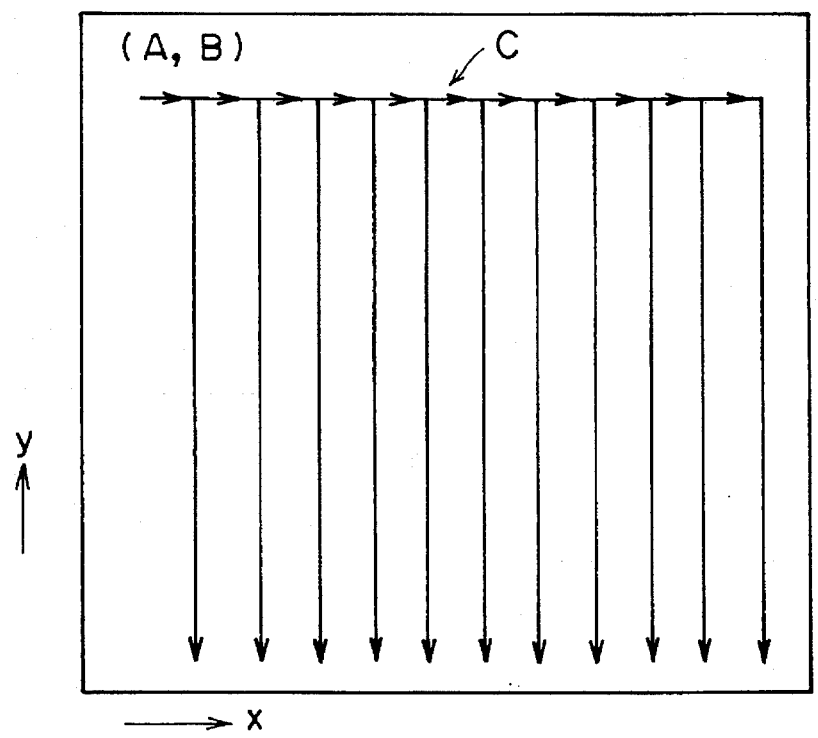
FIG. 12 is a view showing exemplarily a route C starting from a point (A, B)
Figure 13:
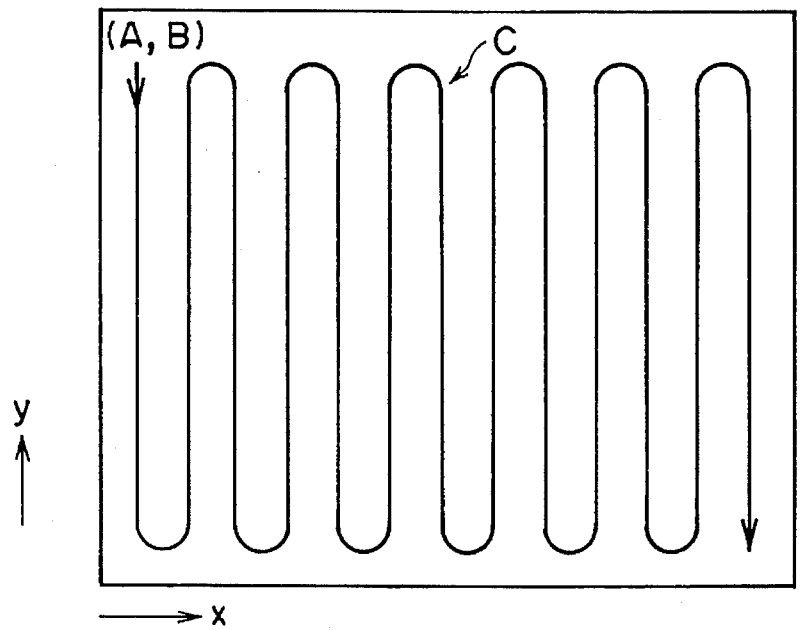
FIG. 13 is a view showing exemplarily a route C starting from a point (A, B)
Figure 14:
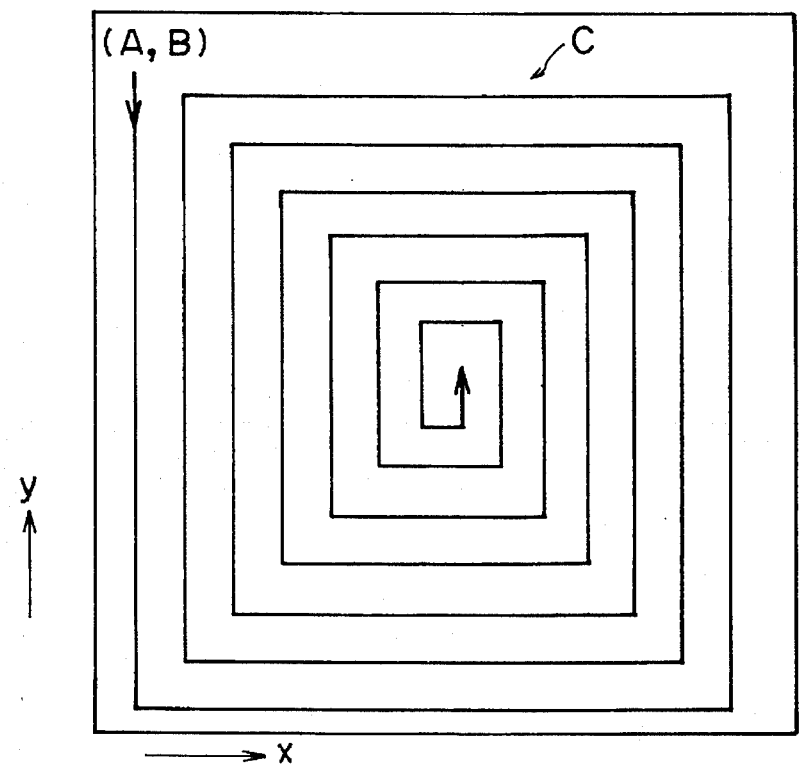
FIG. 14 is a view showing exemplarily a route C starting from a point (A, B)

FIG. 10 is a view showing a step by which the step (7_3) in the flowchart of FIG. 7 can be replaced, in a case where material having a known shear modulus $G_0$ is put on a point (A, B). When the initial value for S is given by $S=\ln G_0$, the logarithm of the shear modulus G(x, y) at the point (x, y), that is, S=ln G (x, y) can be calculated (refer to the equation (43)).

FIGS. 11–14 are each a view showing exemplarily a route C starting from a point (A, B). As seen from these figures, it is possible to arbitrarily determine the route C.

Figure 15:
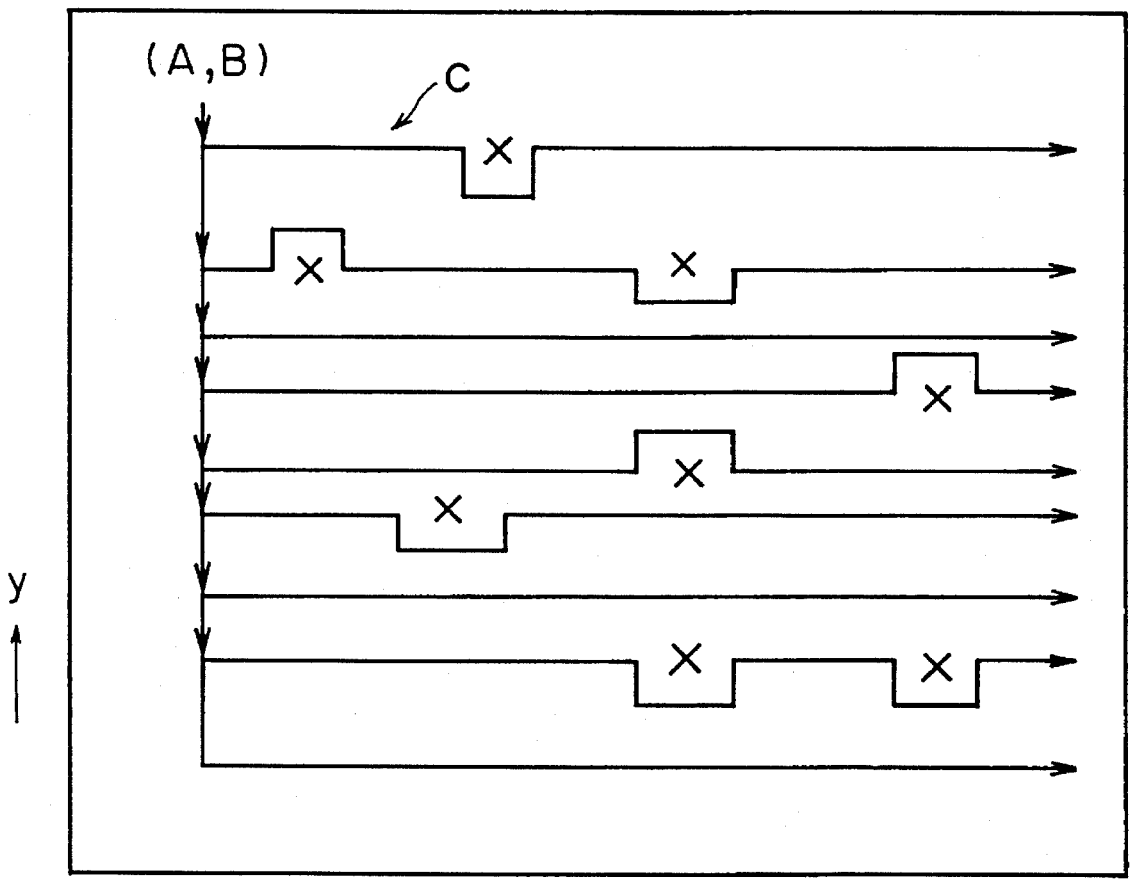
FIG. 15 is a view showing another example of a route C.

FIG. 15 is a view showing another example of a route C. In FIG. 15, the marks x indicate each a point involved in the fact that the denominator det of the integral kernel in the aforementioned equation (41) with respect to the associated point is zero. According to the present embodiment, the route C is adaptively determined, while avoiding a point, det=0. In this manner, in a case where the route C is determined so as to avoid the point, det=0, the step (7_5) in the embodiments shown in FIGS. 7 and 9 may be omitted.

Figure 16A:
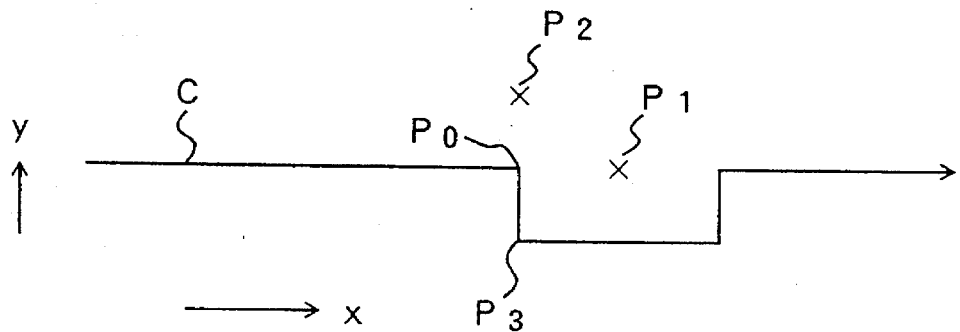
FIGS. 16 (A)–(B) are views useful for explaining a technique of determining a route C, while avoiding a point, det=0, by way of example.
Figure 16B:
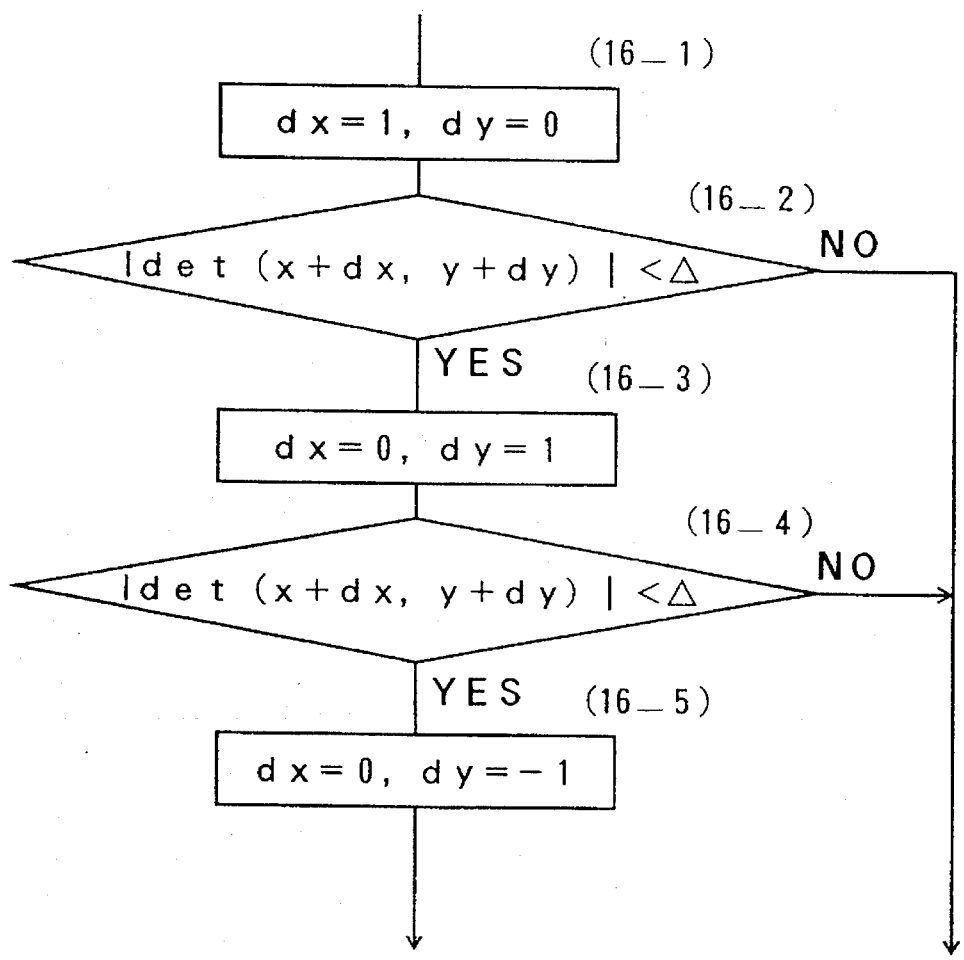

FIGS. 16 (A)–(B) are views useful for explaining a technique of determining a route C, while avoiding a point, det=0, by way of example.

Now, there will be described, by way of example, as shown in FIG. 16 (A), such a case that the process advances in the x-direction and encounters the point, det=0.

As shown in FIG. 16 (B), in step (16_1), there is given the increment vector (dx, dy)=(1, 0) with respect to the x-direction. In step (16_2), it is determined as to the increased point (x+dx, y+dy) whether or not |det|<Δ. If |det|≧Δ, the process advances in the x-direction without change of the travelling direction. On the other hand, in a case where the process advances to the point of |det|<Δ such as the advancement from the point $P_0$ to the point $P_1$, the program proceeds to step (16_3) in which the process advances in the y-direction toward the point $P_2$ on the basis of the point $P_0$ with the increment vector (dx, dy)=(0, 1). It is determined as to the point $P_2$ also whether or not |det|<Δ. If |det|<Δ also with respect to point $P_2$, then the process advances in the minus y-direction toward the point $P_3$ on the basis of the point $P_0$ with the increment vector (dx, dy)= (0, −1).

In this manner, there will be formed a route C avoiding the point, |det|<Δ, when an obstacle (|det|<Δ) exists in the travelling direction, through modifying the travelling direction.

Figure 17:
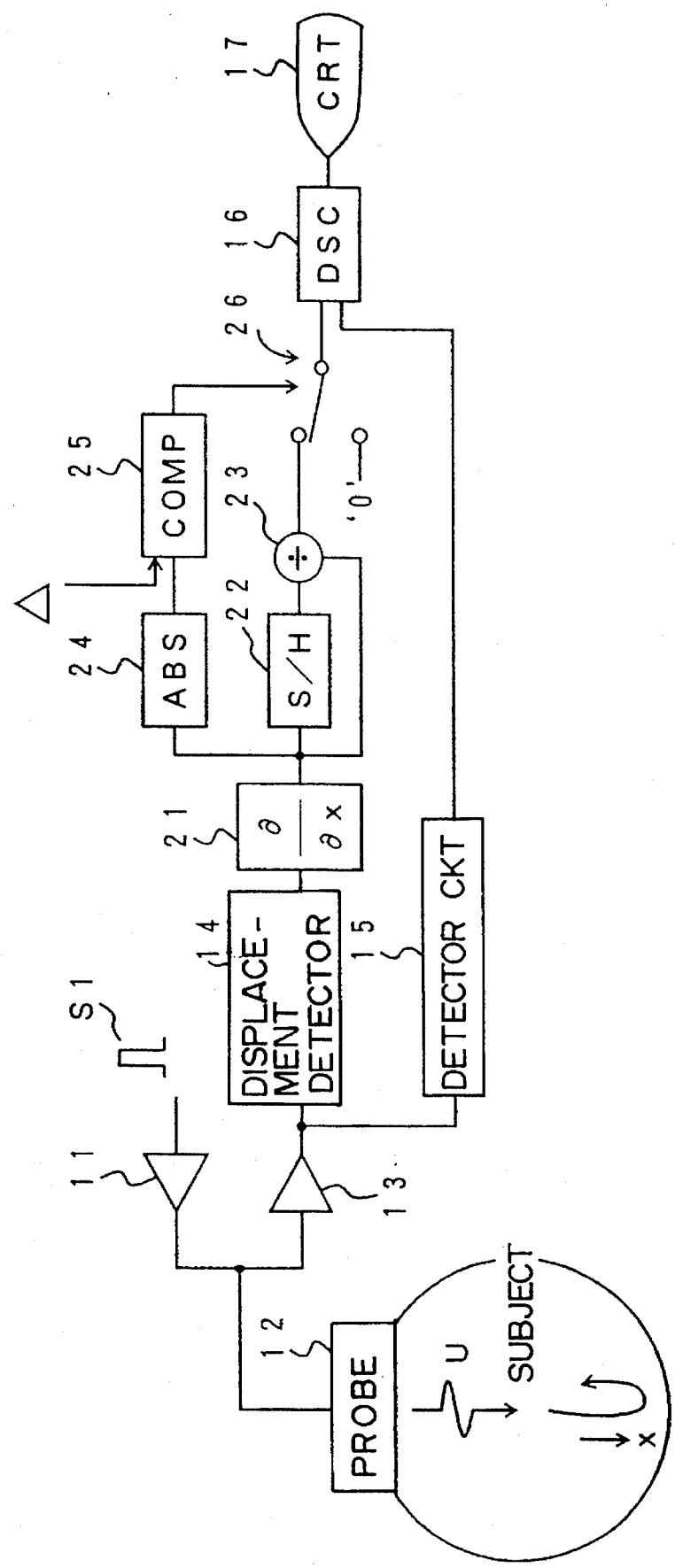
FIG. 17 is a block diagram showing the basic arrangement of constituents of an ultrasonic diagnostic system into which an elasticity measuring apparatus according to the first embodiment concerning a device of the present invention is incorporated.

FIG. 17 is a block diagram showing the basic arrangement of constituents of an ultrasonic diagnostic system into which an elasticity measuring apparatus according to the first embodiment concerning a device of the present invention is incorporated.

When an ultrasonic transmitted signal S1 is inputted to a pulser 11, a high voltage pulse is applied from the pulser 11 to a piezoelectric ultrasonic transducer (not illustrated) with which a probe 12 is equipped, so that an ultrasonic pulse U is radiated from the transducer toward the inside of the subject or the human body under examination. The ultrasonic pulse U advances within the subject in a predetermined direction (defined as the x-direction), while being reflected on tissues within the subject. The reflected ultrasounds are received by the transducer and converted into electric signals, which electric signals are passed via a receiving amplifier 13 to a displacement detecting means 14 and a detector circuit 15.

The displacement detecting means 14 detects displacement $U_x$ (x) on the respective points in the x-direction toward which the ultrasonic pulse advances within the subject while the ultrasonic pulse is transmitted and received a plurality of number of times in the same direction within the subject. As a way of detection of the displacement $U_x$ (x), there are known various techniques, for example, a Doppler effect, a cross-correlation, a phase-tracking, etc. The technique of detection of the displacement itself is not essential to the present invention. Accordingly, the detailed description of detection of the displacement will be omitted.

The received signal, which is passed via the receiving amplifier 13, is also inputted to the detector circuit 15 which detects the entered received signal. In the detector circuit 15, tomographic images of the subject are issued through transmitting ultrasounds from the probe 12 in the various directions, for example, on a sheet of FIG. 17, within the subject, and receiving the reflected ultrasounds by the probe 12.

The detector circuit 15, mechanism of transmission and reception of ultrasounds and an arrangement of an ultrasonic diagnostic system in its entirety are of a well known technology, and in addition they are not directly involved in the present invention. Hence, the more detailed description of those will be omitted.

A signal representative of a tomographic image of the subject, which is issued by the detector circuit 15, is applied to a digital scan converter 16 and converted into a signal for use in display. Thus, the tomographic image of the subject is displayed on a screen of a CRT display device 17.

On the other hand, the displacement $U_x$ (x) along the straight line extending in the x-direction within the subject, which has been detected in the displacement detecting means 14, is inputted to a differentiator 21 to perform a differential operation, so that strain $\epsilon_{xx}$ (x) involved in the x-direction is detected.

$$\epsilon_{xx}(x)=(\delta/\delta x)u_x(x)$$

As the differentiator 21, in case that an analog signal is treated, for example, an analog differential filter may be adopted, and in case that a digital signal is treated, for example, a digital filter may be adopted.

Of the strain $\epsilon_{xx}$ (x) determined by the differentiator 21, strain $\epsilon_{xx}$ (A) involved in the reference point (A) is inputted to a sample hold circuit 22 and stored therein. As the sample hold circuit 22, in case that an analog signal is treated, for example, a sample hold circuit adapted for holding the analog signal may be adopted, and in case that a digital signal is treated, for example, a register adapted for storing the digital signal may be adopted.

The strain $\epsilon_{xx}$ (A) involved in the point (A), which is stored in the sample hold circuit 22, and the distortion $\epsilon_{xx}$ (x) involved in the subsequent points (x) are inputted to a divider 23 to perform operation $\epsilon_{xx}$ (A)/$\epsilon_{xx}$ (x). This is equivalent to the ratio of the shear modulus G(x) at the point x to the shear modulus G(A) at the point A, or G(x)/G(A), which is operated on the basis of the equation (23).

$$G(x)/G(A)=\epsilon_{xx}(A)/\epsilon_{xx}(x)$$

The strain $\epsilon_{xx}$ (x) outputted from the differentiator 21 is inputted to an absolute value circuit 24 to compute the absolute value |$\epsilon_{xx}$(x)| of the strain $\epsilon_{xx}$ (x). The absolute value |$\epsilon_{xx}$ (x)| is supplied to a comparator 25 to compare it with a threshold Δ. A switching circuit 26 is controlled in accordance with an output of the comparator 25. If |$\epsilon_{xx}$ (x)|≧Δ, the output of the divider 23 is inputted to a digital scan converter 16, while if |$\epsilon_{xx}$ (x)|<Δ, the switching circuit 26 is switched to supply the value "0" instead of the output of the divider 23 to the digital scan converter 16. The absolute value circuit 24, the comparator 25 and the switching circuit 26 are provided for the purpose of avoiding such a situation that the value of $\epsilon_{xx}$ (A)/$\epsilon_{xx}$ (x), which is computed by the divider 23, will overflow owing to the fact that the value of the strain $\epsilon_{xx}$ (x) is too small.

The above-mentioned ratio G(x)/G(A), which is computed by the divider 23, is converted by the digital scan converter 16 into a signal for use in display. For example, such an information is superposed on the tomographic image of the subject, so that the hard portion within the subject will be color-displayed with the luminance according to the hardness of the associated portion.

Figure 18:
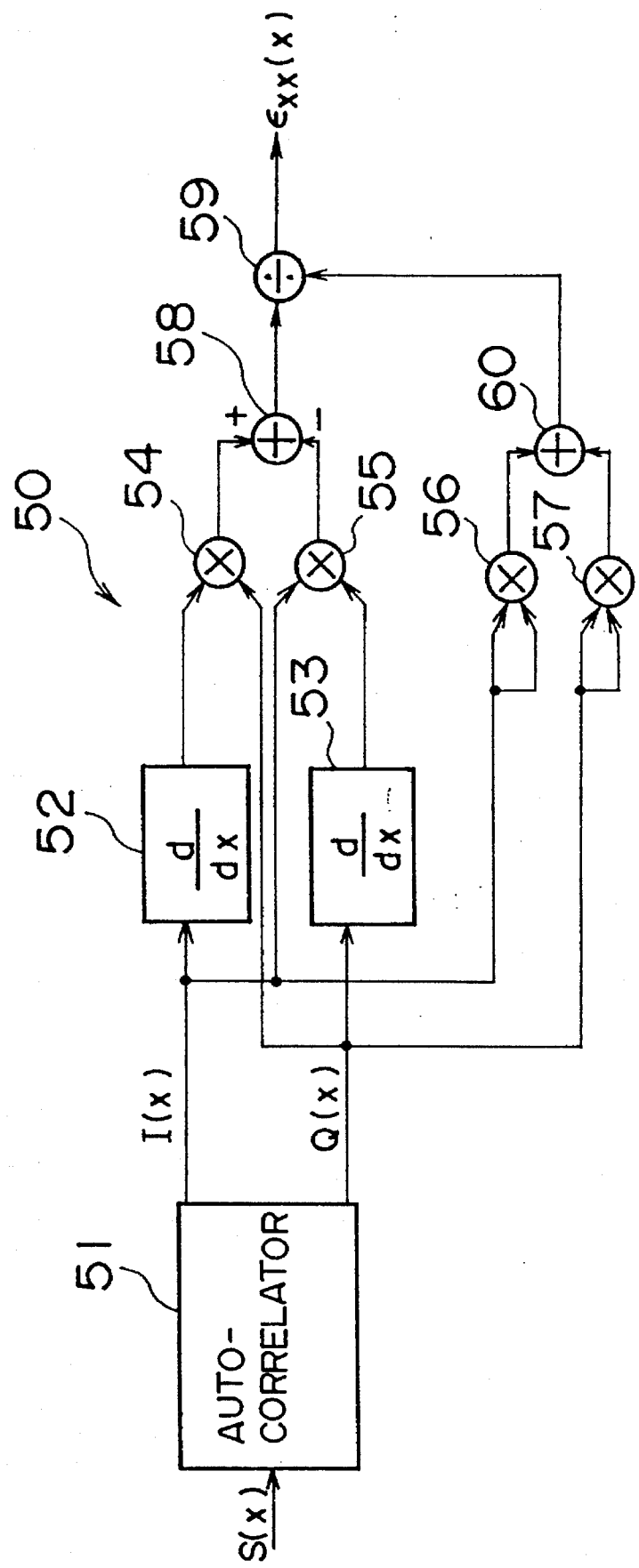
FIG. 18 is a block diagram showing a strain detecting circuit by way of example.

FIG. 18 is a block diagram showing a strain detecting circuit, by way of example, with which the displacement detecting means 14 and the differentiator 21 in the embodiment shown in FIG. 17 can be replaced.

The strain detecting circuit 50 shown in FIG. 18 is based on the principle which will be described hereinafter.

An arithmetic operation for complex auto-correlation of the received signal S (x) as to a predetermined direction (x-direction) is performed to determine an inphase component I(x) and a quadrature component Q (x). Through determination of the inverse tangent (arctan) of the ratio of these components, the displacement $U_x$ (x) involved in the x-direction at the point x is obtained in the form of the following equation:

$$U_x(x) = \arctan\{I(x)/Q(x)\}$$

While, the strain $\epsilon_{xx}$ (x) involved in the x-direction at the point x is given by $$\epsilon_{xx}(x) = d\, U_x(x)/dx$$

The above expression can be rewritten as follows:

$$\begin{aligned}\epsilon_{xx}(x) &= (d/dx) \arctan\{I(x)/Q(x)\} \quad (46)\\ &= (d/dx)\{I(x)/Q(x)\}/[1 + \{I(x)/Q(x)\}^2]\\ &= [\{dI(x)/dx\} \cdot Q(x) - I(x) \cdot \{dQ(x)/dx\}]/\\ &\quad [\{I(x)\}^2 + \{Q(x)\}^2]\end{aligned}$$

The strain detecting circuit 50 shown in FIG. 18 performs an arithmetic operation on the basis of the modified formula noted above, and detects the strain $\epsilon_{xx}$ (x) without detecting the displacement $U_x$ (x).

The received signal S (x) passing through the receiving amplifier 13 (refer to FIG. 17) is inputted to an auto-correlator 51 of the strain detecting circuit 50 shown in FIG. 18. The auto-correlator 51 performs an arithmetic operation for complex auto-correlation of the received signal S (x). The auto-correlator 51 itself is well known, and thus the illustration of the arrangement of constituents thereof and the associated description will be omitted.

The auto-correlator 51 issues an inphase component I(x) and a quadrature component Q (x), which are passed via differentiators 52 and 53 to multipliers 54 and 55, respectively, and in addition directly to the multipliers 55 and 54, respectively. Further, these components I(x) and a quadrature component Q (x) are supplied to multipliers 56 and 57, respectively, so that $\{I(x)\}^2 + \{Q(x)\}^2$ is detected.

The signals $\{dI(x)/dx\} \cdot Q(x)$, and $I(x) \cdot \{d Q(x)/dx\}$, which are outputted from the multipliers 54 and 55, respectively, are subjected to the subtraction process by a subtracter 58, and then inputted to a divider 59. While the signals $\{I(x)\}^2$, and $\{Q(x)\}^2$, which are outputted from multipliers 56 and 57, respectively, are added to each other by an adder 59, and then inputted to the divider 59. Thus, divider 59 may output the strain $\epsilon_{xx}$ (x) detected on the basis of the formula (46).

In this manner, it is also possible to detect the strain without detecting the displacement $U_x$ (x).

Figure 19:
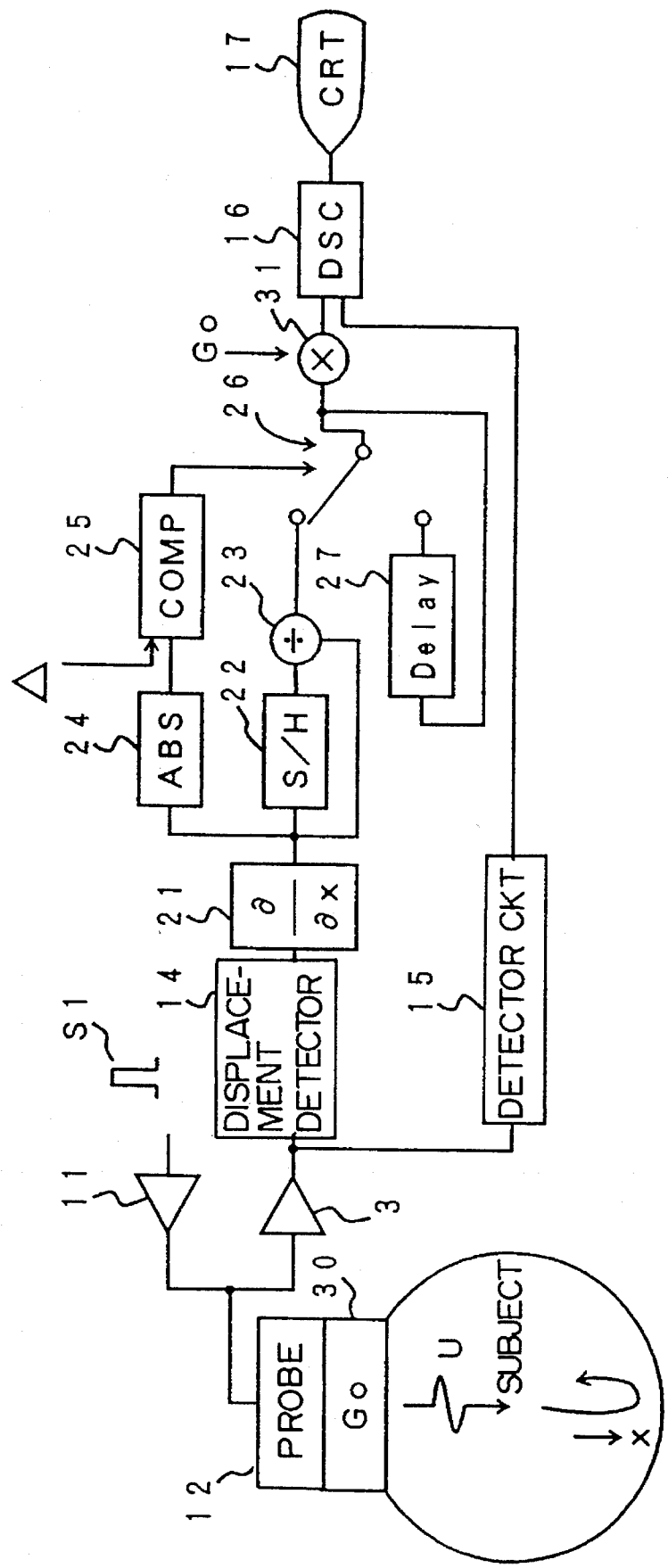
FIG. 19 is a block diagram showing the basic arrangement of constituents of an ultrasonic diagnostic system into which an elasticity measuring apparatus according to the second embodiment concerning a device of the present invention is incorporated.

FIG. 19 is a block diagram showing the basic arrangement of constituents of an ultrasonic diagnostic system into which an elasticity measuring apparatus according to the second embodiment concerning a device of the present invention is incorporated. In the following figures, the same parts are denoted by the same reference numbers as those of FIG. 19.

Specifically, to transmit the ultrasonic pulse U to the inside of the subject, material 30 having a known shear modulus $G_0$ is sandwiched between the probe 12 and the subject and then the ultrasonic pulse U is radiated. Here, a specified point inside of the material 30 is selected as a reference point A.

A multiplier 31 for multiplying by the shear modulus $G_0$ of the material 30 is set up before the digital scan converter 16 with respect to the signal flow. In this manner, the shear modulus G(x) at the point x is determined in accordance with the formula (25), so that the shear modulus G(x) can be displayed on a screen of a CRT display 17. Specifically, the system may be so arranged that for example, when it is desired that a distribution of hardness of the tomographic image is seen in its entirety, such information is superposed on the tomographic image of the subject, so that the hard portion inside of the subject will be color-displayed with the luminance according to the hardness of the associated portion, whereas when it is desired that the shear modulus G(x) at the specified point x within the tomographic image is seen, the shear modulus G(x) involved in that point is displayed with the numeral through moving a cursor to that point.

According to the embodiment shown in FIG. 19, there is provided a delay circuit 27 before the switching circuit 26 with respect to the signal flow. The reason why the delay circuit 26 is provided is that when the comparator determines $|\epsilon_{xx}(x)| < \Delta$, the shear modulus G(x−dx) at a point (x−dx) near the point x is used as the shear modulus G(x) at the point x.

Figure 20:
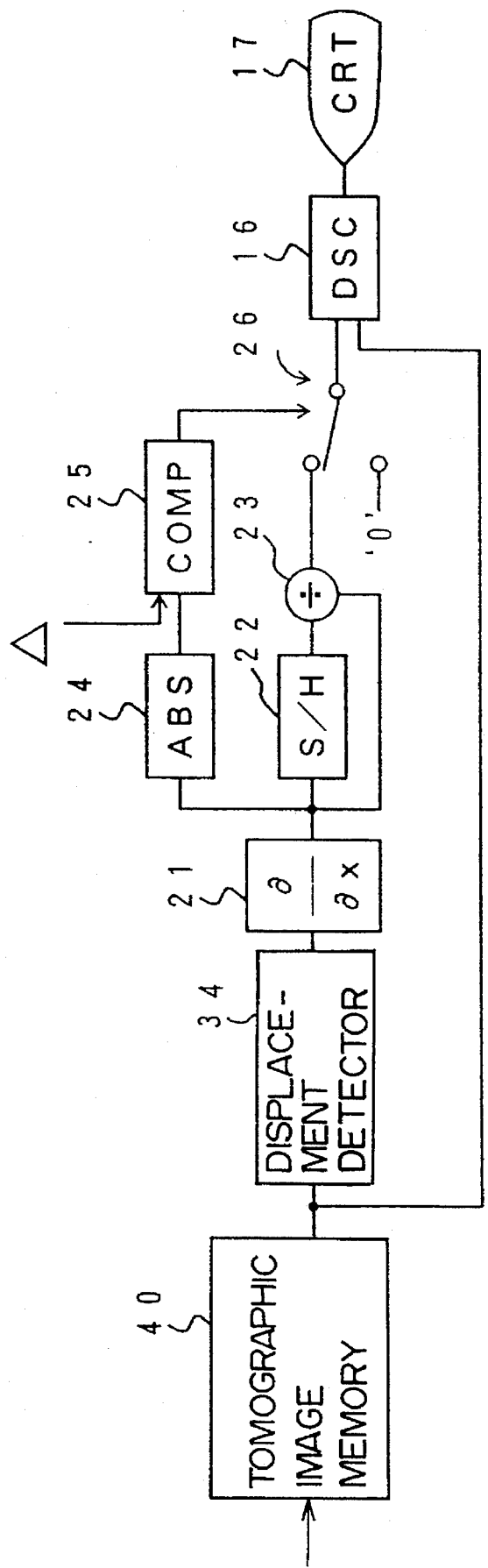
FIG. 20 is a block diagram showing the basic arrangement of constituents of an image display apparatus into which an elasticity measuring apparatus according to the third embodiment concerning a device of the present invention is incorporated.

FIG. 20 is a block diagram showing the basic arrangement of constituents of an image display apparatus into which an elasticity measuring apparatus according to the third embodiment concerning a device of the present invention is incorporated.

The image display apparatus shown in FIG. 20 has a tomographic image memory 40 adapted for temporarily storing an image signal representative of a tomographic image of the subject, which image signal will be transmitted to the image display apparatus. As means for generating such an image signal, there is no particular restriction. It is acceptable to adopt, as such an image signal, for example, the signal outputted from the detector circuit 15 of the ultrasonic diagnostic system as shown in FIGS. 17 and 19, or signals which will be obtained by the use of other apparatuses such as an X-ray CT, an MRI and etc.

The tomographic image memory 40 stores a plurality of image signals each representative of a tomographic image measured at intervals of time $\Delta t$. The displacement detecting means 34 detects the displacement of the tomographic image measured every time $\Delta t$ in accordance with the image signals. A way of detection of the displacement is not restricted. It is possible, for example, to detect the displacement by means of performing an arithmetic operation for mutual-correlation between two tomographic images measured with an interval of time $\Delta t$.

While the ultrasonic diagnostic system as shown in FIGS. 17 and 19 is provided with the detector circuit 15 for producing the image signal and the displacement detecting means 14 as well, in which the displacement is detected directly from the prior signal involved in producing the image signal, according to the embodiment shown in FIG. 20, the displacement detecting means 34 detects the displacement $U_x$ (x) on a predetermined straight line (x-direction) on the basis of the image signals each representative of the associated tomographic image, which image signals are stored in the tomographic image memory 40.

Figure 21:
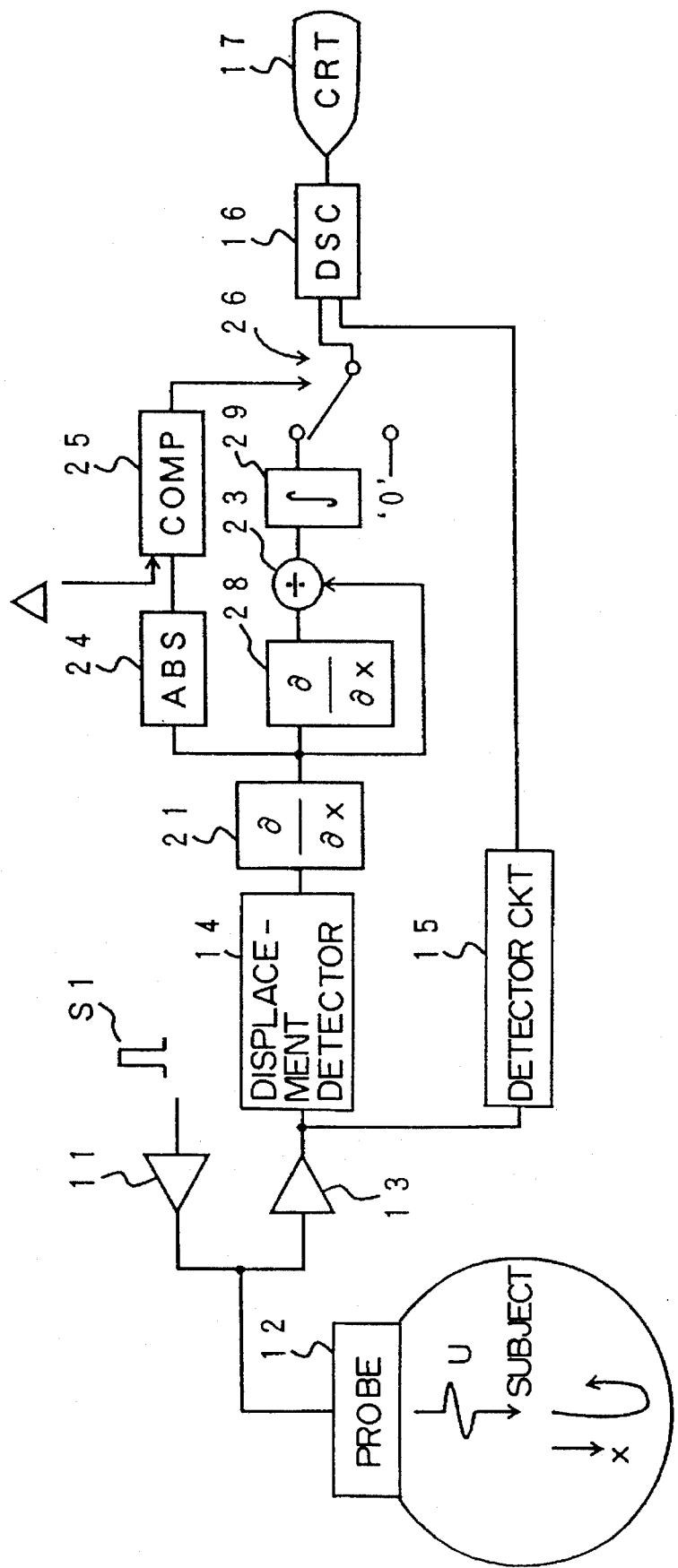
FIG. 21 is a block diagram showing the basic arrangement of constituents of an ultrasonic diagnostic, system into which an elasticity measuring apparatus according to the fourth embodiment concerning a device of the present invention is incorporated.

FIG. 21 is a block diagram showing the basic arrangement of constituents of an ultrasonic diagnostic system into which an elasticity measuring apparatus according to the fourth embodiment concerning a device of the present invention is incorporated.

The strain $\epsilon_{xx}$ (x) detected in the differentiator 21, which is involved in the point x on a straight line extending to the direction in which the ultrasonic pulse advances within the subject, is inputted to an additional differentiator 28 to detect a differential coefficient $\epsilon_{xx}$ (x), x of the strain $\epsilon_{xx}$ (x). The strain $\epsilon_{xx}$ (x) and the differential coefficients $\epsilon_{xx}$ (x), $_x$ are inputted to the divider 23 to perform the arithmetic operation for $\epsilon_{xx}$ (x), $_x/\epsilon_{xx}$ (x). A result of the arithmetic operation is inputted to an integrator 29 to perform the integration from the reference point A to the point x along the straight line. In this manner, there is determined logarithm of the ratio of the shear modulus G(x) at the point x to the shear modulus G(A) at the point A in accordance with the aforementioned equation (21), that is, ln {G(x)/G(A)}.

Figure 22A:
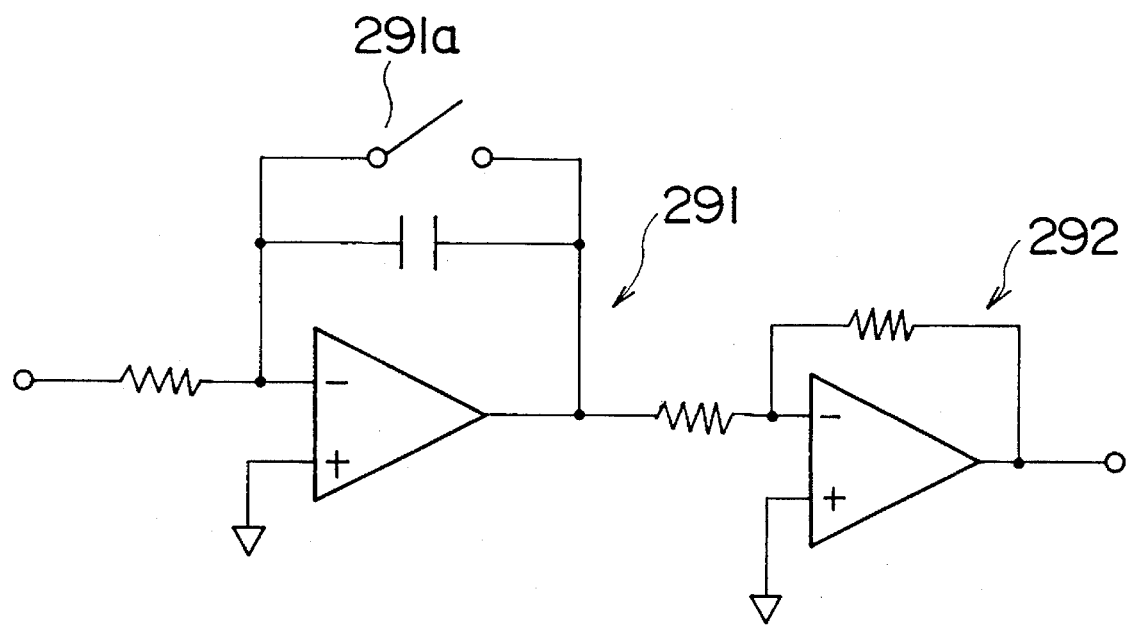
Figure 22B:
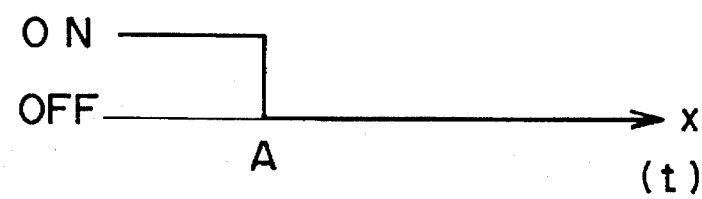
FIG. 22B is a view useful for explanation of operation of the integrator shown in FIG. 22A.

FIG. 22A is a block diagram showing an integration circuit by way of example in a case where an analog signal is dealt with. FIG. 22B is a view useful for explanation of operation of the integration circuit shown in FIG. 22A.

In a case where an analog signal is dealt with, it is possible to arrange an integrator, as shown in FIG. 22A, which comprises an integration circuit 291 using an operational amplifier, and a sign inverter 292 for inverting the sign of an output signal of the integration circuit 291. To provide a point A as a starting point of the integration, the integration circuit 291 is equipped with a switch 291a. As shown in FIG. 22B, the switch 291a is kept closed until the signal corresponding to the point A is inputted, and the switch 291a is opened at the time when the signal corresponding to the point A is inputted. When the ultrasonic pulse U is radiated to the inside of the subject, the deeper the the ultrasounds go into the subject, the later the reflected ultrasounds are received. Thus, the distance in the x-direction inside of the subject is in proportion to the receiving time x of the signal. Consequently, an arithmetic operation for the integration, taking the point A as the starting point, may be performed through opening the switch 291a at the time point corresponding to the point A.

Figure 23A:
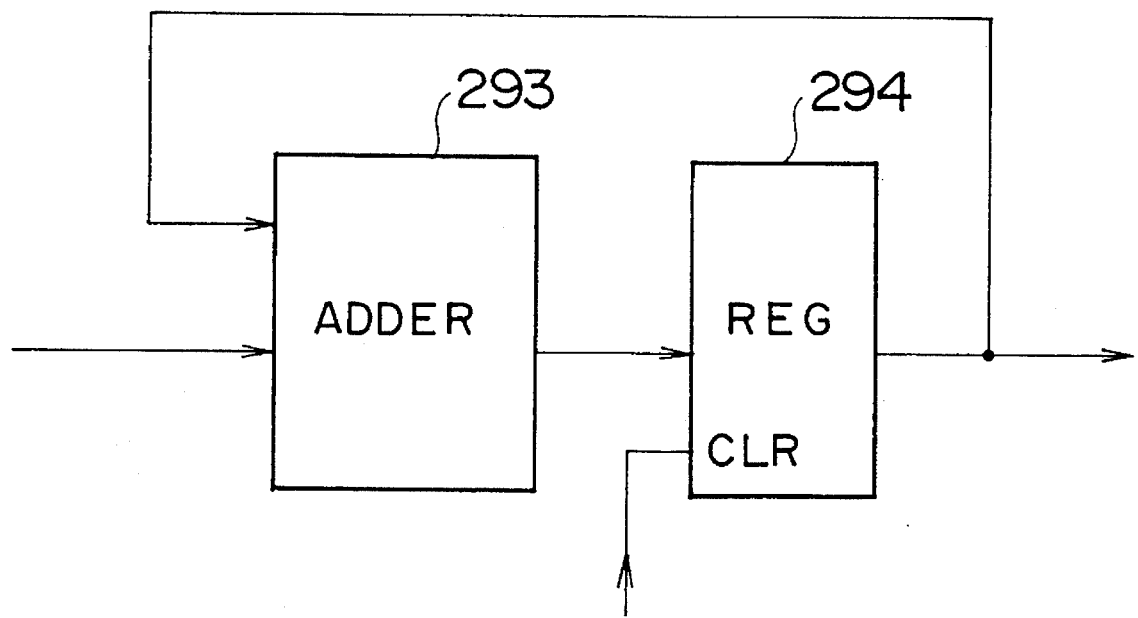
Figure 23B:
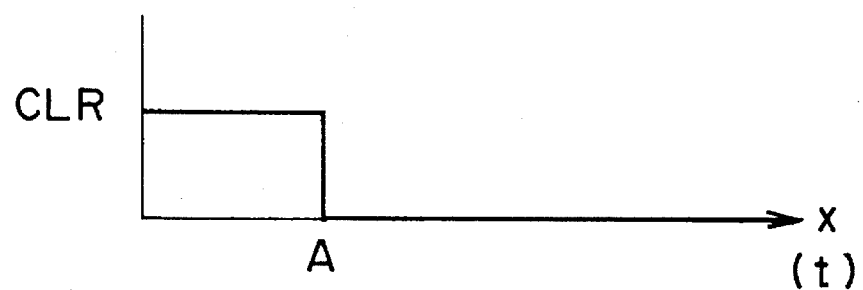
FIG. 23B is a view useful for explanation of operation of the integrator shown in FIG. 23A.

FIG. 23A is a block diagram showing an integrator by way of example in a case where a digital signal is dealt with. FIG. 23B is a view useful for explanation of operation of the integrator shown in FIG. 23A.

Digital signals are inputted to an adder 293 as shown in FIG. 23A on a time sequential basis. An output of the adder 293 is stored in a register 294. The adder 293 serves to add the newly entered value to the old value stored in the register 294 and refresh the register 294 to store the additional result therein. Thus, the register 294 may store the accumulated value of the digital signals sequentially inputted, that is, the integral value. The register 294 has a clear terminal CLR to which as shown in FIG. 23B, a clear signal is being inputted up to the reference point A. At the time point that the signal corresponding to the point A is inputted, the clear is released so as to start the integral as to the input after that point. In this manner, the starting point of the integral is determined.

Figure 24:
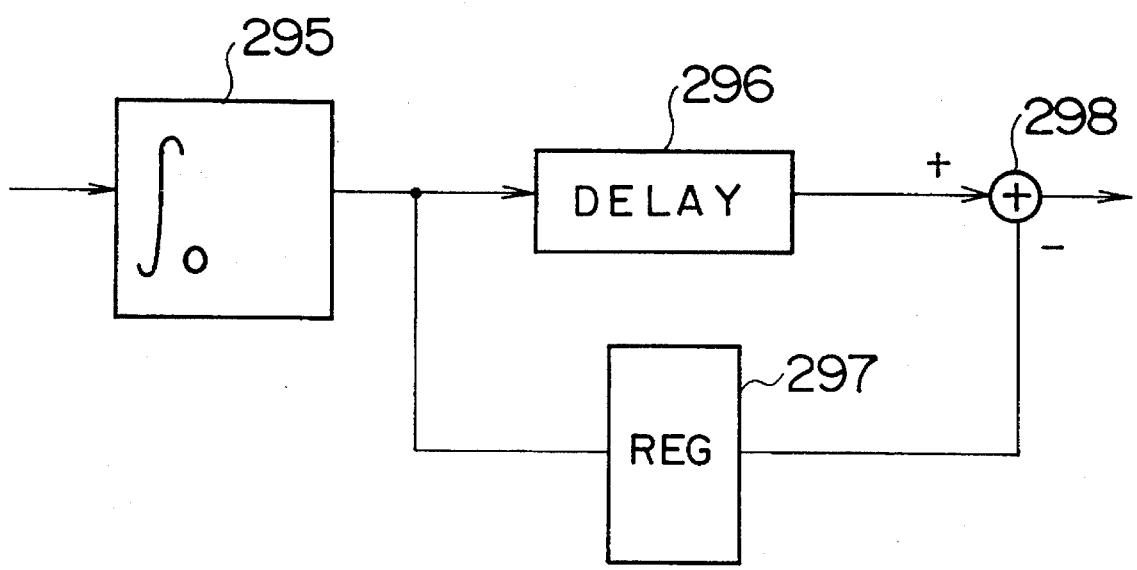
FIG. 24 is a view useful for explaining a scheme in which a starting point of integral of the integrator adapted to deal with the digital signal is optionally determined.

FIG. 24 is a view useful for explaining a scheme in which a starting point of integral of the integrator adapted to deal with the digital signal is optionally determined.

As a general rule, the integral equation of the function f(x) is given by the following expression:

$$\int_A^x f(x)dx = \int_0^x f(x)dx - \int_0^A f(x)dx$$

Hence, it is possible to determine the integral value in a case where the point A is selected as the starting point of the integral, even if the integral does not always start from the point A. An integrator 295 effects an integral taking the origin x=0 as the starting point, so that the integral values are sequentially stored in a delay circuit 296. With respect to the delay circuit 296, a delay time is set up in such a way that after completion of the integral up to the maximum point x=MAX, the delay circuit 296 sequentially outputs the integral values involved in the respective points from the origin x=0 up to the maximum point x=MAX. When the integrator 295 has completed the integral operation as to the respective points up to the point A, the obtained integral value is stored in a register 297. A subtracter 298 subtracts the integral value involved in the point A from the integral values involved in the respective points x which are sequentially outputted from the delay circuit 296.

The integrator 29 shown in FIG. 21 may be constructed with the arrangement shown in FIG. 24. According to such an arrangement, it is possible to optionally set up the reference point A by means of selecting a timing in which the integral value is stored in a register 297.

Figure 25:
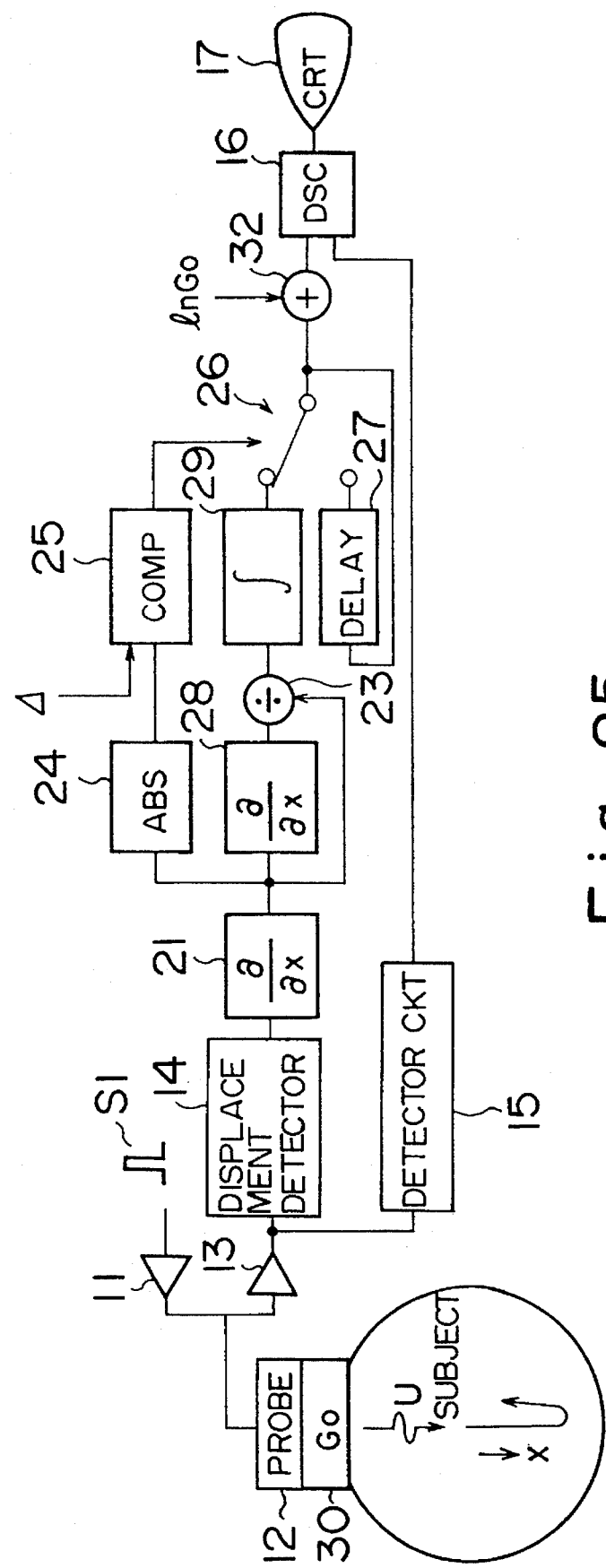
FIG. 25 is a block diagram showing the basic arrangement of constituents of an ultrasonic diagnostic system into which an elasticity measuring apparatus according to the fifth embodiment concerning a device of the present invention is incorporated.

FIG. 25 is a block diagram showing the basic arrangement of constituents of an ultrasonic diagnostic system into which an elasticity measuring apparatus according to the fifth embodiment concerning a device of the present invention is incorporated.

The material 30 having a known shear modulus $G_0$ is sandwiched between the probe 12 and the subject. An adder 32 is connected between the switching circuit 26 and the digital scan converter 16. According to such an arrangement, it is possible to detect logarithm in G(x) of the shear modulus G(x) at the point x in accordance with the aforementioned equation (24).

Figure 26:
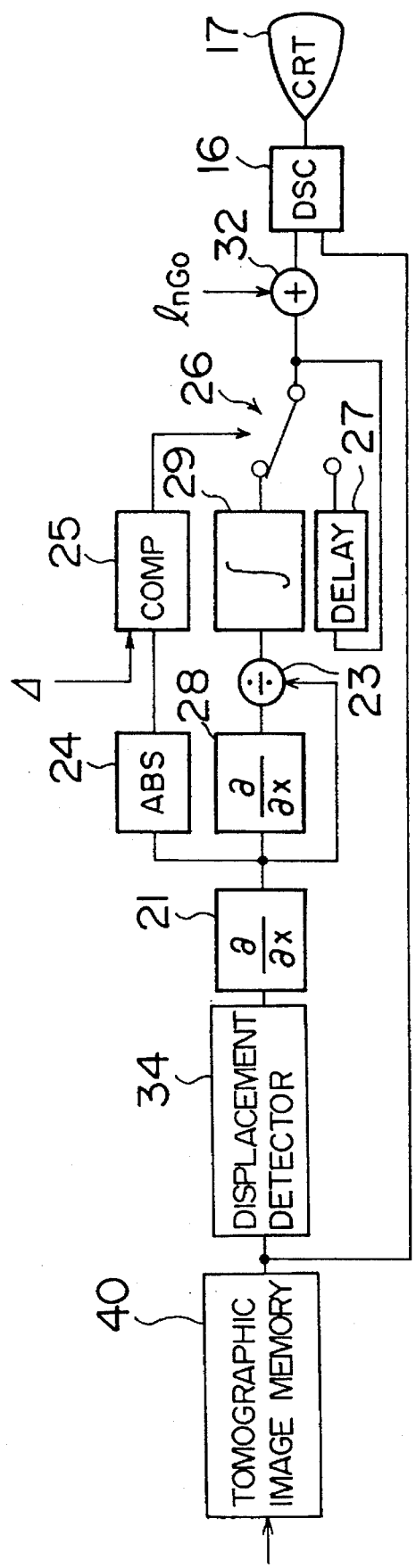
FIG. 26 is a block diagram showing the basic arrangement of constituents of an ultrasonic diagnostic system into which an elasticity measuring apparatus according to the sixth embodiment concerning a device of the present invention is incorporated.

FIG. 26 is a block diagram showing the basic arrangement of constituents of an ultrasonic diagnostic system into which an elasticity measuring apparatus according to the sixth embodiment concerning a device of the present invention is incorporated.

The present embodiment is equivalent to the combination of the embodiment shown in FIG. 20 and the embodiment in FIG. 25. Hence, the detailed description of the present embodiment will be omitted.

Figure 27:
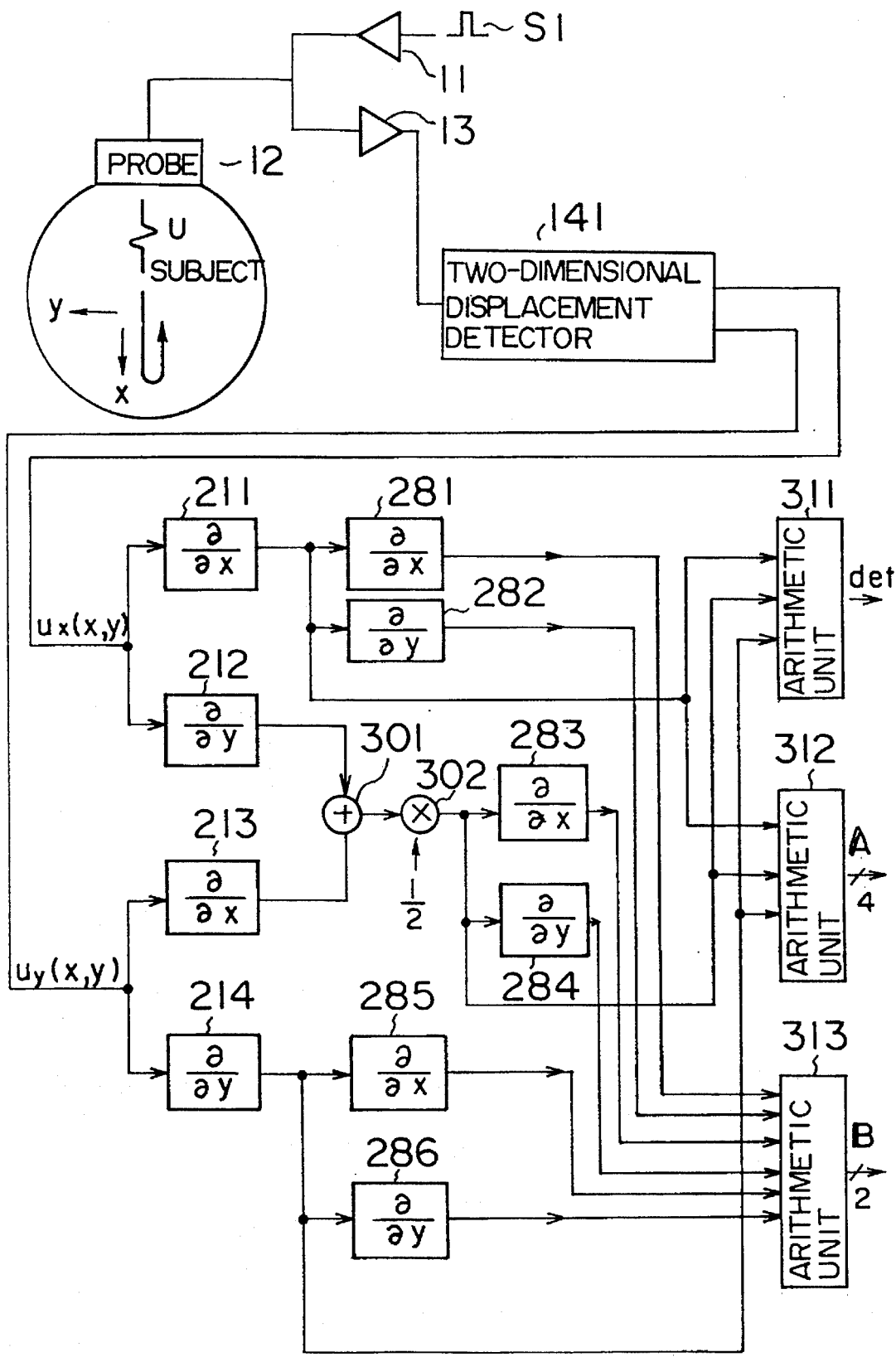
FIG. 27 is a block diagram showing the basic arrangement of constituents of the first half part of a signal processing apparatus of an ultrasonic diagnostic system into which an elasticity measuring apparatus according to the seventh embodiment concerning a device of the present invention is incorporated.

FIG. 27 is a block diagram showing the basic arrangement of constituents of the first half part of a signal processing apparatus of an ultrasonic diagnostic system into which an elasticity measuring apparatus according to the seventh embodiment concerning a device of the present invention is incorporated.

The ultrasonic pulse U is radiated from the probe 12 in the various directions on a predetermined two-dimensional plane spreading inside of the subject, so that the inside of the subject is scanned with ultrasonic pulse beams.

The received signal, which is passed via the receiving amplifier 13, is inputted to two-way displacement detecting means 141. The two-way displacement detecting means 141 detects an x-direction displacement $U_x$ (x, y), and a y-direction displacement $U_y$ (x, y) on the points in the two-dimensional plane. These displacements $U_x$ (x, y) and $U_y$ (x, y) can be determined by means of applying, for example, a two-dimensional cross-correlation scheme and the like. A way of detection of the displacements $U_x$ (x, y) and $U_y$ (x, y) are well known, and the technique of detection of the displacement itself is not essential to the present invention. Accordingly, the detailed description of detection of the displacement will be omitted.

The displacements $U_x(x, y)$ and $U_y(x, y)$ on the points in the two-dimensional plane, which have been detected in the two-way displacement detecting means 141, are inputted to two pairs of differentiators 211, 212; and 213, 214, respectively, so that $\epsilon_{xx}(x, y)$, $u_{xy}(x, y)$, $u_{yx}(x, y)$ and $\epsilon_{yy}(x, y)$ are computed in accordance with the following equations:

$$\epsilon_{xx}(x,y)=(\delta/\delta x)u_x(x, y)$$

$$u_{xy}(x,y)=(\delta/\delta y)u_x(x, y)$$

$$u_{yx}(x,y)=(\delta/\delta x)u_y(x, y)$$

$$\epsilon_{yy}(x,y)=(\delta/\delta y)u_y(x, y)$$

The strain $\epsilon_{xx}(x, y)$, which is outputted from the differentiator 211, is inputted to differentiators 281 and 282, and arithmetic units 311 and 312 as well. The differentiators 281 and 282 perform an arithmetic operation for the differential coefficients $\epsilon_{xx}(x,y)_{,x}$ and $\epsilon_{xx}(x,y)_{,y}$ of the strain $\epsilon_{xx}(x,y)$, respectively.

$$\epsilon_{xx}(x,y)_{,x}=(\delta/\delta x)\epsilon_{xx}(x,y)$$

$$\epsilon_{xx}(x,y)_{,y}=(\delta/\delta y)\epsilon_{xx}(x,y)$$

The strains $u_{x,y}(x,y)$ and $u_{yx}(x,y)$, which are outputted from the differentiators 212 and 213, respectively, are added each other by an adder 301 and then multiplied by ½ with a multiplier 302, so that the strain $\epsilon_{xy}=\{u_{xy}(x,y)+u_{yx}(x,y)\}/2$ can be determined. This result is inputted to two differentiators 283 and 284, and the arithmetic units 311 and 312 as well. The differentiators 283 and 284 differentiate the strain $\epsilon_{xy}(x,y)$ in both the x-direction and the y-direction, and perform an arithmetic operation for the differential coefficients $\epsilon_{xy}(x,y)_{,x}$ and $\epsilon_{xy}(x,y)_{,y}$, respectively.

$$\epsilon_{xy}(x,y)_{,x}=\epsilon_{yx}(x,y)_{,x}=(\delta/\delta x)\{u_{xy}(x, y)+u_{yx}(x, y)\}/2$$

$$\epsilon_{xy}(x, y)_{,y}=\epsilon_{yx}(x, y)_{,y}=(\delta/\delta y)\{u_{xy}(x,y)+u_{yx}(x,y)\}/2$$

The strain $\epsilon_{yy}(x, y)$, which is outputted from the differentiator 214, is inputted to differentiators 285 and 286, and arithmetic units 311 and 312 as well. The differentiators 285 and 286 perform an arithmetic operation for the differential coefficients $\epsilon_{yy}(x,y)_{,x}$ and $\epsilon_{yy}(x,y)_{,y}$, respectively.

$$\epsilon_{yy}(x,y)_{,x}=(\delta/\delta x)\epsilon_{yy}(x,y)$$

$$\epsilon_{yy}(x,y)_{,y}=(\delta/\delta y)\epsilon_{yy}(x,y)$$

The differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{yy}(x,y)_{,y}$, which are obtained by the differentiators 281, 282; 283, 284; and 285, 286, are inputted to an arithmetic unit 313.

The arithmetic unit 311 performs the arithmetic operation for the following formula on the basis of the entered strains, $\epsilon_{xx}(x,y)$, $\epsilon_{xy}(x,y)=\epsilon_{yx}(x,y)$, and $\epsilon_{yy}(x,y)$.

$$\det=\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)$$

where "det" corresponds to the denominator of the integral kernel of the equation (41).

The arithmetic unit 312 performs the arithmetic operation for four elements constituting the following matrix on the basis of the entered distortions, $\epsilon_{xx}(x,y)$, $\epsilon_{xy}(x,y)=\epsilon_{yx}(x,y)$ and $\epsilon_{yy}(x,y)$.

$$A = \begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}$$

The arithmetic unit 313 performs the arithmetic operation for two elements constituting the following matrix (vector) on the basis of the entered differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{yy}(x,y)_{,y}$.

$$B = \begin{pmatrix} \{2\epsilon_{xx}(x,y)+\epsilon_{yy}(x,y)\}_{,x}+\epsilon_{xy}(x,y)_{,y} \\ \epsilon_{yx}(x,y)_{,x}+\{\epsilon_{xx}(x,y)+2\epsilon_{yy}(x,y)\}_{,y} \end{pmatrix}$$

Figure 28:
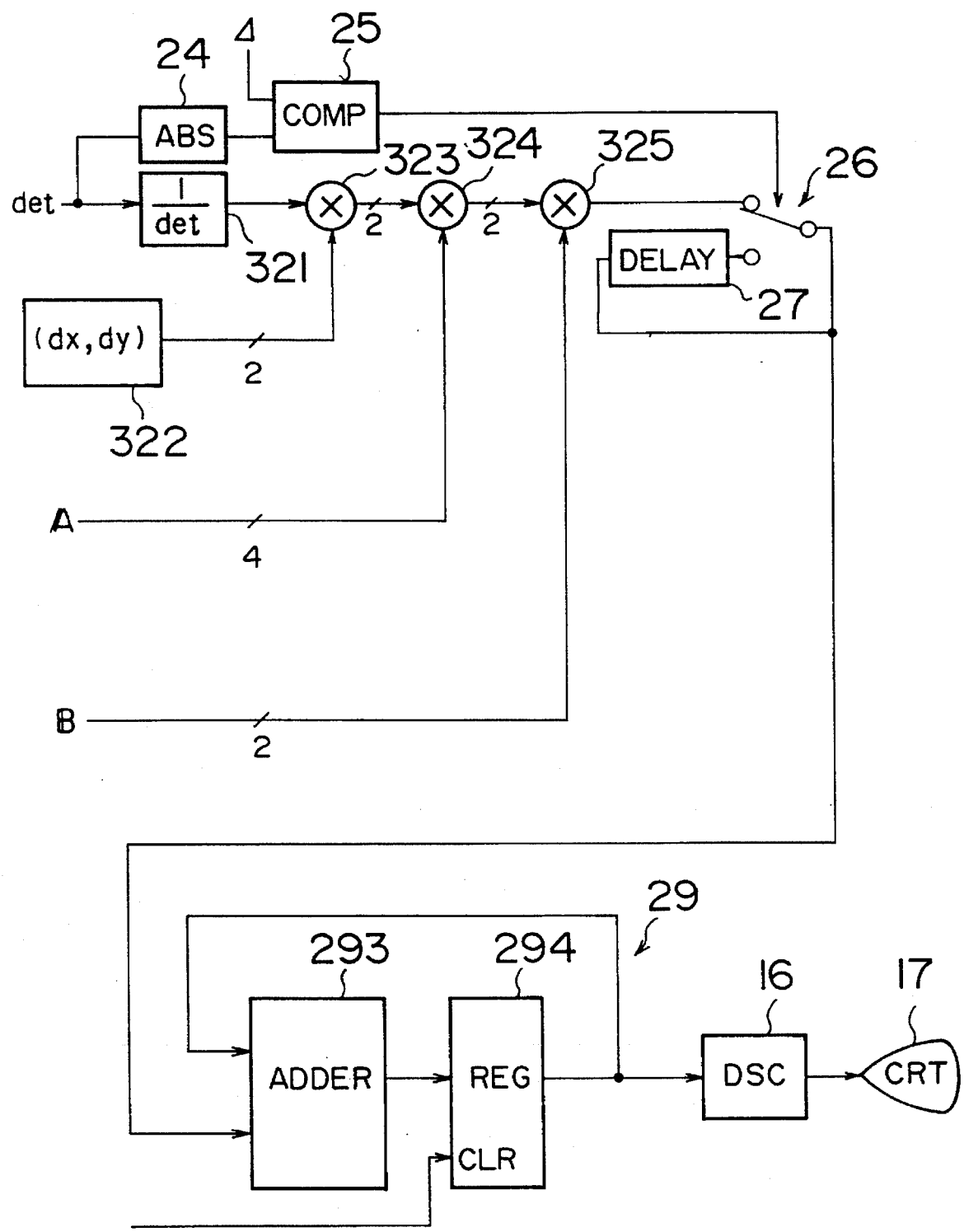
FIG. 28 is a block diagram showing the basic arrangement of constituents of the latter half part of a signal processing apparatus of an ultrasonic diagnostic system into which an elasticity measuring apparatus according to the seventh embodiment concerning a device of the present invention is incorporated.

FIG. 28 is a block diagram showing the basic arrangement of constituents of the latter half part of a signal processing apparatus of an ultrasonic diagnostic system into which an elasticity measuring apparatus according to the seventh embodiment concerning a device of the present invention is incorporated.

The denominator det detected by the arithmetic unit 311 is inputted to the reciprocal arithmetic unit 321 to be converted into 1/det, and then passed to a multiplier 323 to which the infinitely small increment vector (dx, dy) stored in a ROM 322 is also inputted. An output of the multiplier 323 is passed to the next stage of multiplier 324 to be multiplied by the matrix A. An output of the multiplier 324 is passed to the next stage of multiplier 325 to be multiplied by the matrix (vector) B. In this manner, the value of the integral kernel of the aforementioned equation (41) can be determined with respect to the point (x, y). The value of the integral kernel is integrated by the integrator 29, so that logarithm of the ratio of the shear modulus G(x, y) at the point (x, y) to the shear modulus G(A, B) at the reference point (A, B), that is, ln $\{G(x, y)/G(A, B)\}$ can be determined, as shown in the equation (42).

The thus determined logarithm, ln $\{G(x, y)/G(A, B)\}$, of the ratio of the shear modulus at the point (x, y) on a two-dimensional plane inside of the subject is passed via the digital scan converter 16 to the CRT display 17, so that the logarithmic information can be displayed on a screen of the CRT display 17. Specifically, the system may be so arranged that for example, similar to the arrangement shown in FIG. 17, there is provided the detector circuit 15, and when it is desired that a distribution of hardness of the tomographic image is seen in its entirety, such information is superposed on the tomographic image of the subject, so that the hard portion inside of the subject will be color-displayed with the luminance according to the hardness of the associated portion.

Figure 29:
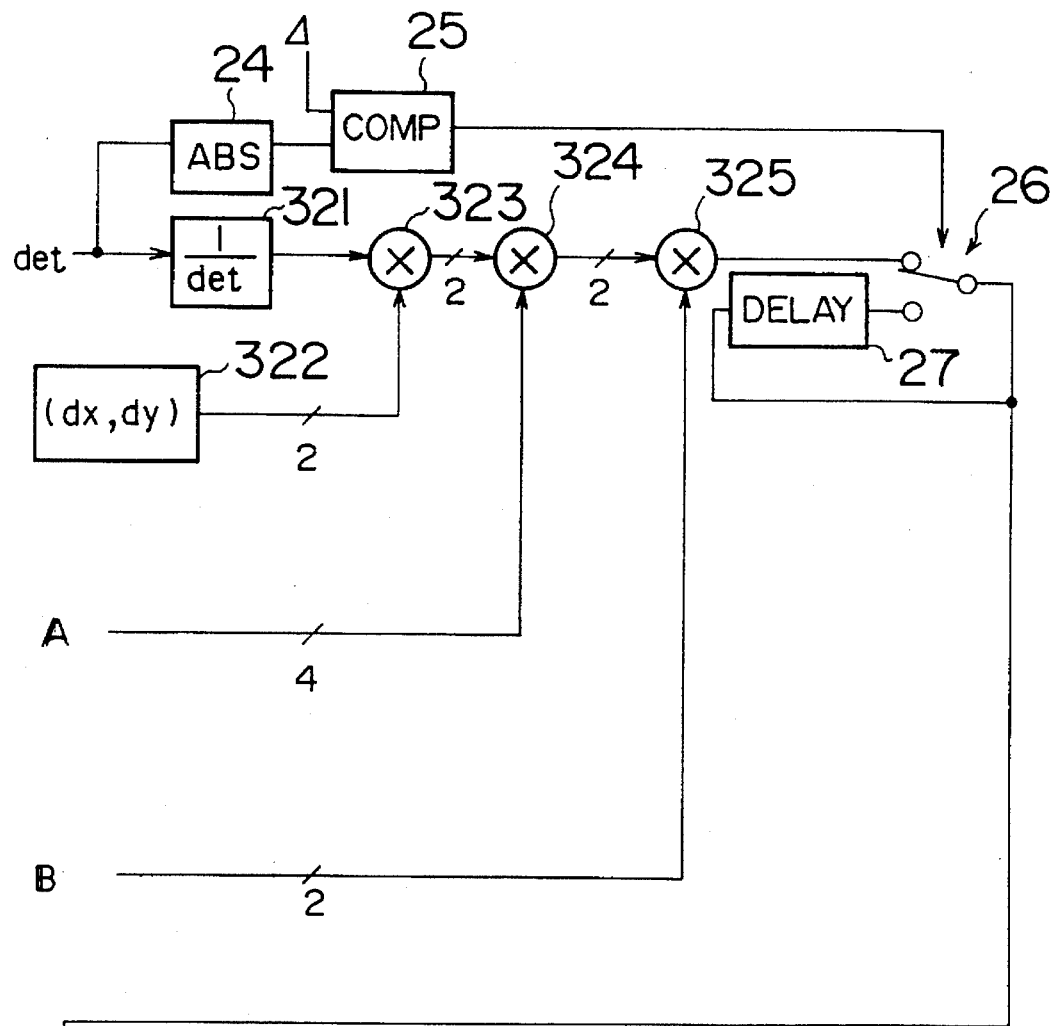
FIG. 29 is a block diagram showing the basic arrangement of constituents of an ultrasonic diagnostic system into which an elasticity measuring apparatus according to the eighth embodiment concerning a device of the present invention is incorporated.
Figure 29:
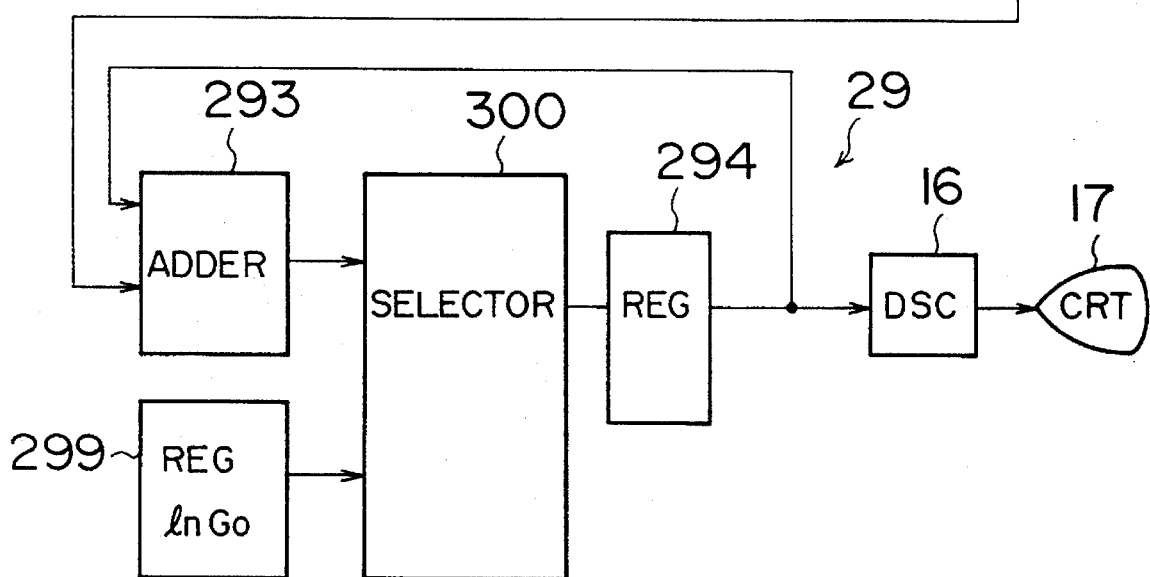

FIG. 29 is a block diagram showing the basic arrangement of constituents of the latter half part of a signal processing apparatus of an ultrasonic diagnostic system into which an elasticity measuring apparatus according to the eighth embodiment concerning a device of the present invention is incorporated. Regarding the first half part of the signal processing apparatus, the equivalence of the arrangement shown in FIG. 27 may be used. Specifically, to transmit and receive ultrasonic acoustic waves, for example, as shown in FIG. 19, material having a known shear modulus $G_0$ is sandwiched between the probe 12 and the subject.

In the arrangement of constituents of the device shown in FIG. 29, the different point from that in FIG. 28 resides in the integrator 29. A register 299 stores beforehand logarithm in $G_0$ of the shear modulus of the material sandwiched between the probe 12 and the subject. To conduct the integral operation, the value ln $G_0$ is transferred through a selector 300 to a register 294, and thereafter the selector 300 is switched so as to receive an output of an adder 293. The adder 293 is set up with providing the value in $G_0$ as an initial value and is operative to add to the initial value input values supplied through the switching circuit 26 on a cumulative basis. In this manner, as shown in the aforementioned equation (43), it is possible to determine logarithm ln G (x, y) of the shear modulus involved in the point (x, y).

While the embodiments shown in FIGS. 27–29 relate to an example in which the elasticity measuring apparatus according to the present invention is incorporated into the ultrasonic diagnostic system, it is of course acceptable to apply the two-dimensional signal processing as shown in FIGS. 27–29 to for example the image display apparatus as described referring to FIG. 20.

Further, while all the above-described embodiments are involved in detecting the shear modulus G, its logarithm ln G, or the ratio of such shear modulus to that on the reference point, it is of course acceptable to provide an arrangement in which Young's modulus E rather than the shear modulus is detected. Furthermore, the present invention does not necessarily have to detect the shear modulus, Young's modulus, logarithm of those and the like, and it is sufficient for the present invention to detect data representative of the level of elasticity on the points within the subject.

As described in detail above, according to the present invention, it is possible to know the elastic level of the respective points within the subject only through measuring the distortion of those points, without measuring the stress distribution of those points, thereby contributing to the industrial inspection, the diagnosis of a living body and the like quite a lot.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An elasticity measuring method comprising the steps of:

generating and transmitting ultrasonic waves in a direction along a predetermined straight line extending inside of a subject having a surface;

receiving reflected ultrasonic waves to obtain a received ultrasonic signal;

detecting the ratio of elastic value of the surface-to-elastic value of inside of the subject, which is based on the received ultrasonic signal and which is representative of level of elasticity involved in a reference point on the predetermined straight line extending inside of the subject and a predetermined observation point on the straight line, respectively, by detecting the ratio of strain of the surface-to-strain of the inside of the subject, which is involved in said reference point and said observation point, respectively, with respect to the direction toward which the straight line extends, wherein it is determined whether an absolute value of the strain on the observation point exceeds a predetermined threshold, and if the absolute value is less than the threshold, a predetermined value by which the ratio of strain of the surface-to-strain of the inside of the subject involved in said reference point and said observation point is replaced is associated with said observation point, instead of said ratio of strain of the surface-to-strain of the inside of the subject.

2. An elasticity measuring method comprising the steps of:

generating and transmitting ultrasonic waves in a direction along a predetermined straight line extending inside of a subject having a surface;

receiving reflected ultrasonic waves to obtain an ultrasonic received signal, wherein:

a reference member, of which elastic value representative of a level of elasticity is known, is disposed on a reference point on the predetermined straight line extending inside of the subject, and an elastic value on a predetermined observation point on the straight line within the subject is detected on the basis of the ratio of strain of the surface-to-strain of the inside of the subject, which is involved in said reference point and said observation point, respectively, with respect to a direction toward which the straight line extends, and the elastic value of said reference member, wherein it is determined whether an absolute value of the strain on the observation point exceeds a predetermined threshold, and if the absolute value is less than the threshold, a predetermined value by which the ratio of strain of the surface-to-strain of the inside of the subject involved in said reference point and said observation point is replaced is associated with said observation point, instead of said ratio of strain of the surface-to-strain of the inside of the subject.

3. An elasticity measuring method comprising the steps of:

generating and transmitting ultrasonic waves in a direction along a predetermined straight line extending inside of a subject;

receiving reflected ultrasonic waves to obtain a received ultrasonic signal;

detecting strain $\epsilon_{xx}(x)$ based on the received ultrasonic signal, as to points on the predetermined straight line extending inside of the subject from a reference point A up to a predetermined observation point X, with respect to a direction toward which the straight line extends, and a differential coefficient $\epsilon_{xx}(x),_x$ of the strain $\epsilon_{xx}(x)$ with respect to the direction toward which the straight line extends, and detecting an integral value of the ratio of the strain $\epsilon_{xx}(x)$ to the differential coefficient $\epsilon_{xx}(x),_x$ along the straight line from the reference point A up to the observation point X, whereby the ratio of elastic value-to-elastic value, which are representative of levels of elasticity involved in the reference point A and the observation point X, respectively, is detected.

4. An elasticity measuring method wherein a reference member, of which elastic value representative of a level of elasticity is known, is disposed on a reference point A on a predetermined straight line-extending inside of a subject, said method comprising the steps of:

generating and transmitting ultrasonic waves in a direction along a predetermined straight line extending inside of the subject;

receiving reflected ultrasonic waves to obtain a received ultrasonic signal;

detecting strain $\epsilon_{xx}(x)$, based on the received ultrasonic signal, as to points on the straight line extending inside of the subject from the reference point A up to a predetermined observation point X, with respect to a direction toward which straight line extends, and a differential coefficient $\epsilon_{xx}(x),_x$ of the strain $\epsilon_{xx}(x)$ with respect to the direction toward which the straight line extends, detecting an integral value of the ratio of the strain $\epsilon_{xx}(x)$ to the differential coefficient $\epsilon_{xx}(x),_x$ along the straight line from the reference point A up to the observation point X, and detecting an elastic value on the observation point X on the basis of both the integral value and the elastic value of said reference member.

5. An elasticity measuring method according to claim 3, wherein it is determined whether absolute values of the strain $\epsilon_{xx}$ (x) on the points x exceed a predetermined threshold, and if an absolute value of strain $\epsilon_{xx}$ ($x_0$) as to a predetermined point $x_0$ of any of the points x is less than the threshold, the ratio of the strain $\epsilon_{xx}$ ($x_0$) as to the predetermined point $x_0$ to the differential coefficient $\epsilon_{xx}$ ($x_0$), $_x$ is replaced by a predetermined value to detect the integral value.

6. An elasticity measuring method according to claim 4, wherein it is determined whether absolute values of the strain $\epsilon_{xx}$ (x) on the points x exceed a predetermined threshold, and if an absolute value of strain $\epsilon_{xx}$ ($x_0$) as to a predetermined point $x_0$ of any of the points x is less than the threshold, the ratio of the strain $\epsilon_{xx}$ ($x_0$) as to the predetermined point $x_0$ to the differential coefficient $\epsilon_{xx}$ ($x_0$), $_x$ is replaced by a predetermined value to detect the integral value.

7. An elasticity measuring method comprising the steps of:

generating and transmitting ultrasonic waves extending inside a subject;

receiving reflected ultrasonic waves to obtain a received ultrasonic signal;

detecting strains, based on the received ultrasonic signal, $\epsilon_{xx}$ (x,y), $\epsilon_{xy}$ (x,y), $\epsilon_{yx}$ (x,y) and $\epsilon_{yy}$ (x,y) as to points (x, y) on an arbitrary route C in a predetermined two-dimensional plane spreading within a subject from a reference point (A, B) up to a predetermined observation point (X,Y), and their associated differential coefficients $\epsilon_{xx}$ (x,y), $_x$; $\epsilon_{xx}$ (x,y), $_y$; $\epsilon_{xy}$ (x,y),$_x$; $\epsilon_{xy}$ (x, y), $_y$; $\epsilon_{yy}$ (x, y), $_x$; $\epsilon_{yy}$ (x, y), $_y$; and detecting a curvilinear integral value on the route C from the reference point (A, B) up to the observation point (X,Y), where the curvilinear integral value is given by the following expression $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)}$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\},_x+\epsilon_{xy}(x,y),_y \\ \epsilon_{yx}(x,y),_x+\{\epsilon_{xx}(x,y)+2\epsilon_{yy}(x,y)\},_y \end{pmatrix}$$

whereby the ratio of elastic value-to-elastic value, which are representative of levels of elasticity involved in the reference point (A, B) and the observation point (X, Y), respectively, is detected.

8. An elasticity measuring method wherein a reference member, of which elastic value representative of a level of elasticity is known, is disposed on a reference point (A, B) in a predetermined two-dimensional plane spreading with a subject, said method comprising the steps of:

generating and transmitting ultrasonic waves extending inside the subject;

receiving reflected ultrasonic waves to obtain a received ultrasonic signal;

detecting strains, based on the received ultrasonic signal, $\epsilon_{xx}$ (x,y), $\epsilon_{xy}$ (x,y), $\epsilon_{yx}$ (x,y) and $\epsilon_{yy}$ (x,y) as to points (x, y) on an arbitrary route C in the two-dimensional plane from a reference point (A, B) up to a predetermined observation point (X,Y), and their associated differential coefficients $\epsilon_{xx}$ (x,y), $_x$; $\epsilon_{xx}$ (x,y), $_y$; $\epsilon_{xy}$ (x,y), $_x$; $\epsilon_{xy}$ (x, y), $_y$; $\epsilon_{yy}$ (x,y), $_x$; $\epsilon_{yy}$ (x, y), $_y$;

detecting a curvilinear integral value on the route C from the reference point (A, B) up to the observation point (X,Y), the curvilinear integral value being given by the following expression; and $$-\int_C \frac{1}{\{2\epsilon_{xx}(x,y)+\epsilon_{yy}(x,y)\}\cdot\{\epsilon_{xx}(x,y)+2\epsilon_{yy}(x,y)\}-\epsilon_{xy}(x,y)\cdot\epsilon_{yx}(x,y)}$$

$$(dx \quad dy)\cdot\begin{pmatrix} \epsilon_{xx}(x,y)+2\epsilon_{yy}(x,y) & -\epsilon_{xy}(x,y) \\ -\epsilon_{yx}(x,y) & 2\epsilon_{xx}(x,y)+\epsilon_{yy}(x,y) \end{pmatrix}\cdot$$

$$\begin{pmatrix} \{2\epsilon_{xx}(x,y)+\epsilon_{yy}(x,y)\},_x+\epsilon_{xy}(x,y),_y \\ \epsilon_{yx}(x,y),_x+\{\epsilon_{xx}(x,y)+2\epsilon_{yy}(x,y)\},_y \end{pmatrix}$$

detecting an elastic value on the observation point (X, Y) on the basis of both the integral value and the elastic value of said reference member.

9. An elasticity measuring method according to claim 7, wherein it is determined whether absolute values of the detonator of the integral kernel of said curvilinear integral, det={2 $\epsilon_{xx}$(x,y)+$\epsilon_{yy}$(x,y)}·{$\epsilon_{xx}$(x,y)+ 2 $\epsilon_{yy}$ (x,y)}−$\epsilon_{xy}$ (x,y)·$\epsilon_{yx}$ (x,y), with respect to the points (x, y) exceed a predetermined threshold, and if the absolute value of a detonator det={2 $\epsilon_{xx}$ ($x_0$,$y_0$)+$\epsilon_{yy}$ ($x_0$,$y_0$)}·{$\epsilon_{xx}$ ($x_0$,$y_0$)+2 $\epsilon_{yy}$ ($x_0$,$y_0$)} −$\epsilon_{xy}$ ($x_0$,$y_0$)· $\epsilon_{yx}$ ($x_0$ ,$y_0$) as to a predetermined point ($x_0$ ,$y_0$) of any of the points (x, y) is less than the threshold, the integral kernel as to the predetermined point ($x_0$ ,$y_0$) is replaced by a predetermined value to detect the integral value.

10. An elasticity measuring method according to claim 8, wherein it is determined whether absolute values of the detonator of the integral kernel of said curvilinear integral, det={2 68 $_{xx}$ (x,y)+$\epsilon_{xx}$ (x,y)}·{$\epsilon_{xx}$ (x,y)+ 2 68 $_{yy}$ (x,y)}−$\epsilon_{xy}$ (x,y)·$\epsilon_{yx}$ (x,y), with respect to the points (x, y) exceed a predetermined threshold, and if the absolute value of a detonator det=(2 68 $_{xx}$ ($x_0$ ,$y_0$)+$\epsilon_{yy}$ ($x_0$,$y_0$)}·{$\epsilon_{xx}$ ($x_0$,$y_0$)+2 68 $_{yy}$ ($x_0$,$y_0$)} −$\epsilon_{xy}$ ($x_0$,$y_0$)·$\epsilon$ $_{yx}$ ($x_0$ ,$y_0$) as to a predetermined point ($x_0$ ,$y_0$) of any of the points (x, y) is less than the threshold, the integral kernel as to the predetermined point ($X_0$,$y_0$) is replaced by a predetermined value to detect the integral value.

11. An elasticity measuring apparatus comprising:

ultrasonic wave transmitting and receiving means for transmitting ultrasonic waves a plurality of number of times in the direction along a predetermined straight line extending inside of a subject and receiving the reflected ultrasonic waves to obtain an ultrasonic received signal;

strain arithmetic means for detecting based on the ultrasonic received signal strains $\epsilon_{xx}$ (X) and $\epsilon_{xx}$ (A) of the subject as to an observation point X and a reference point A on the predetermined straight line, respectively, with respect to a direction toward which the straight line extends;

ratio arithmetic means for detecting the ratio of the strains $\epsilon_{xx}$ (X) and $\epsilon_{xx}$ (A) to determine the ratio of elastic value-to-elastic value, which are representative of levels of elasticity involved in the observation point X and the reference point A, respectively; and display means for displaying the ratio of elastic value-to-elastic value determined by said ratio arithmetic means.

12. An elasticity measuring apparatus comprising:

strain arithmetic means for detecting, based on ultrasonic received signals each representative of a tomographic image measured at intervals of a specified time, which tomographic image is involved in a predetermined two-dimensional plane spreading within a subject, strains $\epsilon_{xx}$ (X) and $\epsilon_{xx}$ (A) of the subject as to an observation point X and a reference point A in the two-dimensional plane, respectively, with respect to a direction toward which a straight line coupling the observation point X and the reference point A extends;

ratio arithmetic means for detecting the ratio of the strains $\epsilon_{xx}$ (X) and $\epsilon_{xx}$ (A) to determine the ratio of elastic value-to-elastic value, which are representative of level of elasticity involved in the observation point X and the reference point A, respectively; and display means for displaying the ratio of elastic value-to-elastic value determined by said ratio arithmetic means.

13. An elasticity measuring apparatus according to claim 11, further comprising determining means for determining whether an absolute value of the strain $\epsilon_{xx}$ (X) on the observation point X exceeds a predetermined threshold, wherein said ratio arithmetic means outputs, if the absolute value is less than the threshold, a predetermined value by which the ratio of strain-to-strain respectively involved in said observation point X and said reference point A is replaced, instead of said ratio of strain-to-strain.

14. An elasticity measuring apparatus according to claim 12, further comprising determining means for determining whether an absolute value of the strain $\epsilon_{xx}$ (X) on the observation point X exceeds a predetermined threshold, wherein said ratio arithmetic means outputs, if the absolute value is less than the threshold, a predetermined value by which the ratio of strain-to-strain respectively involved in said observation point X and said reference point A is replaced, instead of said ratio of strain-to-strain.

15. An elasticity measuring apparatus comprising:

ultrasonic wave transmitting and receiving means for transmitting ultrasonic waves a plurality of number of times in the direction along a predetermined straight line extending inside of a subject and receiving the reflected ultrasonic waves to obtain an ultrasonic received signal;

strain detecting means for detecting strain $\epsilon_{xx}$ (x) as to points on the straight line extending inside of the subject from the reference point A up to a predetermined observation point X, with respect to a direction toward which the straight line extends;

differential coefficient arithmetic means for differentiating the strain $\epsilon_{xx}$ (x) in the direction toward which the straight line extends to detect a differential coefficient $\epsilon_{xx}$ (x), $_x$ of the strain $\epsilon_{xx}$ (x) with respect to the direction toward which the straight line extends;

ratio arithmetic means for detecting an integral value of the ratio of the strain $\epsilon_{xx}$ (x) to the differential coefficient $\epsilon_{xx}$ (x), $_x$ along the straight line from the reference point A up to the observation point X, so that the ratio of elastic value-to-elastic value, which are representative of levels of elasticity involved in the reference point A and the observation point X, respectively, is detected; and display means for displaying the ratio of elastic value-to-elastic value determined by said ratio arithmetic means.

16. An elasticity measuring apparatus comprising:

strain detecting means for detecting, based on ultrasonic received signals each representative of a tomographic image measured at intervals of a specified time, which tomographic image is involved in a predetermined two-dimensional plane spreading within a subject, strain $\epsilon_{xx}$ (X) of the subject as to points on a straight line coupling a predetermined observation point X and a reference point A in the two-dimensional plane from the reference point A up to the observation point X, with respect to a direction toward which the straight line extends;

differential coefficient arithmetic means for differentiating the strain $\epsilon_{xx}$ (x) in the direction toward which the straight line extends to detect a differential coefficient $\epsilon_{xx}$ (x), $_x$ of the strain $\epsilon_{xx}$ (x) with respect to the direction toward which the straight line extends;

ratio arithmetic means for detecting an integral value of the ratio of the strain $\epsilon_{xx}$ (x) to the differential coefficient $\epsilon_{xx}$ (x), $_x$ along the straight line from the reference point A up to the observation point X, so that the ratio of elastic value-to-elastic value, which are representative of levels of elasticity involved in the reference point A and the observation point X, respectively, is detected; and display means for displaying the ratio of elastic value-to-elastic value determined by said ratio arithmetic means.

17. An elasticity measuring apparatus according to claim 15, further comprising determining means for determining whether absolute values of the strain $\epsilon_{xx}$ (x) on the points x exceed a predetermined threshold, wherein if an absolute value of strain $\epsilon_{xx}$ ($x_0$) as to a predetermined point $x_0$ of any of the points x is less than the threshold, said ratio arithmetic means detects the integral value through replacing the ratio of the strain $\epsilon_{xx}$ ($x_0$) as to the predetermined point $x_0$ to the differential coefficient $\epsilon_{xx}$ ($x_0$), $_x$ by a predetermined value.

18. An elasticity measuring apparatus according to claim 16, further comprising determining means for determining whether absolute values of the strain $\epsilon_{xx}$ (x) on the points x exceed a predetermined threshold, wherein if an absolute value of strain $\epsilon_{xx}$ ($x_0$) as to a predetermined point $x_0$ of any of the points x is less than the threshold, said ratio arithmetic means detects the integral value through replacing the ratio of the strain $\epsilon_{xx}$ ($x_0$) as to the predetermined point $x_0$ to the differential coefficient $\epsilon_{xx}$ ($x_0$), $_x$ by a predetermined value.

19. An elasticity measuring apparatus according to claim 12, further comprising:

preset means for presetting an elastic value involved in the reference point A;

elasticity arithmetic means for detecting an elastic value on the observation point X on the basis of both the ratio of elastic value-to-elastic value and the elastic value involved in the reference point A; and additional display means for displaying the elastic value on the observation point X, wherein said display means is replaced by said additional display means.

20. An elasticity measuring apparatus according to claim 14, further comprising:

preset means for presetting an elastic value involved in the reference point A;

elasticity arithmetic means for detecting an elastic value on the observation point X on the basis of both the ratio of elastic value-to-elastic value and the elastic value involved in the reference point A; and additional display means for displaying the elastic value on the observation point X, wherein said display means is replaced by said additional display means.

21. An elasticity measuring apparatus according to claim 15, further comprising:
   preset means for presetting an elastic value involved in the reference point A;
   elasticity arithmetic means for detecting an elastic value on the observation point X on the basis of both the ratio of elastic value-to-elastic value and the elastic value involved in the reference point A; and
   additional display means for displaying the elastic value on the observation point X,
   wherein said display means is replaced by said additional display means.

22. An elasticity measuring apparatus according to claim 16, further comprising:
   preset means for presetting an elastic value involved in the reference point A;
   elasticity arithmetic means for detecting an elastic value on the observation point X on the basis of both the ratio of elastic value-to-elastic value and the elastic value involved in the reference point A; and
   additional display means for displaying the elastic value on the observation point X,
   wherein said display means is replaced by said additional display means.

23. An elasticity measuring apparatus comprising:
   ultrasonic wave transmitting and receiving means for transmitting ultrasonic waves a plurality of number of times in directions along a plurality of straight lines in a predetermined two-dimensional plane spreading within a subject and receiving the reflected ultrasonic waves to obtain ultrasonic received signals;
   strain detecting means for detecting strains, $\epsilon_{xx}(x,y)$, $\epsilon_{xy}(x,y)$, $\epsilon_{yx}(x,y)$ and $\epsilon_{yy}(x,y)$ as to points (x, y) on an arbitrary route C in a predetermined two-dimensional plane spreading within a subject from a reference point (A, B) up to a predetermined observation point (X,Y);
   differential coefficient arithmetic means for differentiating the strains, $\epsilon_{xx}(x,y)$, $\epsilon_{xy}(x,y)$, $\epsilon_{yx}(x,y)$ and $\epsilon_{yy}(x,y)$ to detect their associated differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{yy}(x,y)_{,y}$;
   ratio arithmetic means for detecting a curvilinear integral value on the route C from the reference point (A,B) up to the observation point (X,Y), where the curvilinear integral value is given by the following expression $$-\int_C \frac{1}{\{2\epsilon_{xx}(x,y) + \epsilon_{yy}(x,y)\} \cdot \{\epsilon_{xx}(x,y) + 2\epsilon_{yy}(x,y)\} - \epsilon_{xy}(x,y) \cdot \epsilon_{yx}(x,y)} \cdot$$

$$(dx \quad dy) \cdot \begin{pmatrix} \epsilon_{xx}(x,y) + 2\epsilon_{yy}(x,y) & -\epsilon_{xy}(x,y) \\ -\epsilon_{yx}(x,y) & 2\epsilon_{xx}(x,y) + \epsilon_{yy}(x,y) \end{pmatrix} \cdot$$

$$\begin{pmatrix} \{2\epsilon_{xx}(x,y) + \epsilon_{yy}(x,y)\}_{,x} + \epsilon_{xy}(x,y)_{,y} \\ \epsilon_{yx}(x,y)_{,x} + \{\epsilon_{xx}(x,y) + 2\epsilon_{yy}(x,y)\}_{,y} \end{pmatrix}$$

whereby the ratio of elastic value-to-elastic value, which are representative of levels of elasticity involved in the reference point (A, B) and the observation point (X, Y), respectively, is detected; and
   display means for displaying the ratio of elastic value-to-elastic value determined by said ratio arithmetic means.

24. An elasticity measuring apparatus comprising:
   strain detecting means for detecting, based on ultrasonic received signals each representative of a tomographic image measured at intervals of a specified time, which tomographic image is involved in a predetermined two-dimensional plane spreading within a subject, strains, $\epsilon_{xx}(x,y)$, $\epsilon_{xy}(x,y)$, $\epsilon_{yx}(x,y)$ and $\epsilon_{yy}(x,y)$ as to points (x, y) on an arbitrary route C in a predetermined two-dimensional plane spreading within a subject from a reference point (A, B) up to a predetermined observation point (X,Y);
   differential coefficient arithmetic means for differentiating the strains, $\epsilon_{xx}(x,y)$, $\epsilon_{xy}(x,y)$, $\epsilon_{yx}(x,y)$ and $\epsilon_{yy}(x,y)$ to detect their associated differential coefficients $\epsilon_{xx}(x,y)_{,x}$, $\epsilon_{xx}(x,y)_{,y}$, $\epsilon_{xy}(x,y)_{,x}$, $\epsilon_{xy}(x,y)_{,y}$, $\epsilon_{yy}(x,y)_{,x}$, $\epsilon_{yy}(x,y)_{,y}$;
   ratio arithmetic means for detecting a curvilinear integral value on the route C from the reference point (A,B) up to the observation point (X,Y), where the curvilinear integral value is given by the following expression $$-\int_C \frac{1}{\{2\epsilon_{xx}(x,y) + \epsilon_{yy}(x,y)\} \cdot \{\epsilon_{xx}(x,y) + 2\epsilon_{yy}(x,y)\} - \epsilon_{xy}(x,y) \cdot \epsilon_{yx}(x,y)} \cdot$$

$$(dx \quad dy) \cdot \begin{pmatrix} \epsilon_{xx}(x,y) + 2\epsilon_{yy}(x,y) & -\epsilon_{xy}(x,y) \\ -\epsilon_{yx}(x,y) & 2\epsilon_{xx}(x,y) + \epsilon_{yy}(x,y) \end{pmatrix} \cdot$$

$$\begin{pmatrix} \{2\epsilon_{xx}(x,y) + \epsilon_{yy}(x,y)\}_{,x} + \epsilon_{xy}(x,y)_{,y} \\ \epsilon_{yx}(x,y)_{,x} + \{\epsilon_{xx}(x,y) + 2\epsilon_{yy}(x,y)\}_{,y} \end{pmatrix}$$

whereby the ratio of elastic value-to-elastic value, which are representative of levels of elasticity involved in the reference point (A, B) and the observation point (X, Y), respectively, is detected; and
   display means for displaying the ratio of elastic value-to-elastic value determined by said ratio arithmetic means.

25. An elasticity measuring apparatus according to claim 23, further comprising determining means for determining whether absolute values of the detonator of the integral kernel of said curvilinear integral, det=$\{2 \epsilon_{xx}(x,y) + \epsilon_{yy}(x,y)\} \cdot \{\epsilon_{xx}(x,y) + 2 \epsilon_{yy}(x,y)\} - \epsilon_{xy}(x,y) \cdot \epsilon_{yx}(x,y)$, with respect to the points (x, y) exceed a predetermined threshold, wherein if the absolute value of a detonator det=$\{2\epsilon_{xx}(x_0, y_0) + \epsilon_{yy}(x_0, y_0)\} \cdot \{\epsilon_{xx}(x_0, y_0) + 2 \epsilon_{yy}(x_0, y_0)\} - \epsilon_{xy}(x_0, y_0) \cdot \epsilon_{yx}(x_0, y_0)$ as to a predetermined point $(x_0, y_0)$ of any of the points (x, y) is less than the threshold, said ratio arithmetic means detects the integral value through replacing the integral kernel as to the predetermined point $(x_0, y_0)$ by a predetermined value.

26. An elasticity measuring apparatus according to claim 24, further comprising determining means for determining whether absolute values of the detonator of the integral kernel of said curvilinear integral, det=$\{2 \epsilon_{xx}(x,y) + \epsilon_{yy}(x,y)\} \cdot \{\epsilon_{xx}(x,y) + 2 \epsilon_{yy}(x,y)\} - \epsilon_{xy}(x,y) \cdot \epsilon_{yx}(x,y)$, with respect to the points (x, y) exceed a predetermined threshold, wherein if the absolute value of a detonator det=$\{2\epsilon_{xx}(x_0, y_0) + \epsilon_{yy}(x_0, y_0)\} \cdot \{\epsilon_{xx}(x_0, y_0) + 2 \epsilon_{yy}(x_0, y_0)\} - \epsilon_{xy}(x_0, y_0) \cdot \epsilon_{yx}(x_0, y_0)$ as to a predetermined point $(x_0, y_0)$ of any of the points (x, y) is less than the threshold, said ratio arithmetic means detects the integral value through replacing the integral kernel as to the predetermined point $(x_0, y_0)$ by a predetermined value.

27. An elasticity measuring apparatus according to claim 23, further comprising:
   preset means for presetting an elastic value involved in the reference point (A, B);
   elasticity arithmetic means for detecting an elastic value on the observation point (X, Y) on the basis of both the ratio of elastic value-to-elastic value and the elastic value involved in the reference point (A, B); and additional display means for displaying the elastic value on the observation point (X, Y), wherein said display means is replaced by said additional display means.

28. An elasticity measuring apparatus according to claim 24, further comprising:

preset means for presetting an elastic value involved in the reference point (A, B);

elasticity arithmetic means for detecting an elastic value on the observation point (X, Y) on the basis of both the ratio of elastic value-to-elastic value and the elastic value involved in the reference point (A, B); and additional display means for displaying the elastic value on the observation point (X, Y), wherein said display means is replaced by said additional display means.

* * * * *

UNITED STATES PATENT AND TRADEMARK OFFICE
CERTIFICATE OF CORRECTION

PATENT NO. : 5,495,771
DATED : March 5, 1996
INVENTOR(S) : Chikayoshi SUMI, et al.

It is certified that error appears in the above-indentified patent and that said Letters Patent is hereby corrected as shown below:

On Title page, under "[75] Inventors:", please delete "2-12,9, Honch, Koganei-shi" and "184".

Column 17, Equation 2, line 1, change "$(\delta/\delta x)$ to --$(\partial/\partial x)$--;
    line 2, change "$(\delta/\delta x)$ to --$(\partial/\partial x)$--; and
    line 3, change "$(\delta/\delta x)$ to --$(\partial/\partial x)$--, both occurrences.
Column 17, Equation 3, line 1, change "$(\delta/\delta x)$ to --$(\partial/\partial x)$--;
    line 2, change "$(\delta/\delta x)$ to --$(\partial/\partial x)$--;
    line 3, change "$(\delta/\delta x)$ to --$(\partial/\partial x)$--;
    line 4, change "$(\delta/\delta x)$ to --$(\partial/\partial x)$--;
    line 5, change "$(\delta/\delta x)$ to --$(\partial/\partial x)$--; and
    line 6, change "$(\delta/\delta x)$ to --$(\partial/\partial x)$--.
Column 20, Equation 1, line 1, change "$(\delta/\delta x)$ to --$(\partial/\partial x)$--;
    line 56, change "68" to --$\varepsilon$--.
Column 25, Equation 1, line 1, change "$(\delta/\delta x)$ to --$(\partial/\partial x)$--;
    line 2, change "$(\delta/\delta x)$ to --$(\partial/\partial x)$--;
    line 3, change "$(\delta/\delta x)$ to --$(\partial/\partial x)$--; and
    line 4, change "$(\delta/\delta x)$ to --$(\partial/\partial x)$--.
Column 25, Equation 2, line 1, change "$(\delta/\delta x)$ to --$(\partial/\partial x)$--; and
    line 2, change "$(\delta/\delta x)$ to --$(\partial/\partial x)$--.
Column 25, Equation 3, line 1, change "$(\delta/\delta x)$ to --$(\partial/\partial x)$--; and
    line 2, change "$(\delta/\delta x)$ to --$(\partial/\partial x)$--.

UNITED STATES PATENT AND TRADEMARK OFFICE
CERTIFICATE OF CORRECTION

PATENT NO. : 5,495,771
DATED : March 5, 1996
INVENTOR(S) : Chikayoshi SUMI, et al.

It is certified that error appears in the above-indentified patent and that said Letters Patent is hereby corrected as shown below:

Column 4, Equation 4, line 1, change "$(\delta/\delta x)$ to --$(\partial/\partial x)$--; and
    line 2, change "$(\delta/\delta x)$ to --$(\partial/\partial x)$--.

Column 27, line 1, after "value" insert --ln--.

Claim 10, Column 30, line 38, change "68", first occurrence, to --$\varepsilon$--;
    line 38, change "$\varepsilon_{xx}$" to --$\varepsilon_{yy}$--;
    line 38, change "68", second occurrence, to --$\varepsilon$--;
    line 41, change "68", first occurrence, to --$\varepsilon$--;
    line 41, change "68", second occurrence, to --$\varepsilon$--.

Signed and Sealed this

Twenty-seventh Day of August, 1996

Attest:

BRUCE LEHMAN

Attesting Officer    Commissioner of Patents and Trademarks